United States Patent
Kim et al.

(10) Patent No.: US 11,864,796 B2
(45) Date of Patent: Jan. 9, 2024

(54) NEEDLE CHANNEL USED FOR HAIR TRANSPLANTER AND NEEDLE CHANNEL BUNDLE HAVING THE NEEDLE CHANNELS

(71) Applicant: OHDAE CORPORATION, Daegu (KR)

(72) Inventors: Byoung Sul Kim, Gyeongsangbuk-do (KR); Tae Seong Lee, Daegu (KR)

(73) Assignee: OHDAE CORPORATION, Daegu (KR)

( * ) Notice: Subject to any disclaimer, the term of this patent is extended or adjusted under 35 U.S.C. 154(b) by 562 days.

(21) Appl. No.: 17/106,183

(22) Filed: Nov. 30, 2020

(65) Prior Publication Data

US 2021/0077148 A1 Mar. 18, 2021

Related U.S. Application Data

(63) Continuation of application No. PCT/KR2019/006203, filed on May 23, 2019.

(30) Foreign Application Priority Data

Jul. 2, 2018 (KR) ........................ 10-2018-0076789

(51) Int. Cl.
*A61B 17/34* (2006.01)
*A61B 17/00* (2006.01)

(52) U.S. Cl.
CPC ..................... *A61B 17/3468* (2013.01); *A61B 2017/00752* (2013.01)

(58) Field of Classification Search
CPC ................ A61B 17/0482; A61B 17/06; A61B 17/06061; A61B 17/062; A61B 17/3468; A61B 17/34; A61B 2017/00752
See application file for complete search history.

(56) References Cited

U.S. PATENT DOCUMENTS 4,451,254 A * 5/1984 Dinius .............. A61M 37/0069
221/232
5,817,120 A 10/1998 Rassman
(Continued)

FOREIGN PATENT DOCUMENTS

KR 20-0368968 Y1 12/2004
KR 100958727 B1 5/2010
(Continued)

OTHER PUBLICATIONS

The extended European Search Report for EP Application No. 19830312.5 dated Jan. 26, 2022, citing the above reference(s).
(Continued)

*Primary Examiner* — Kelly J Bekker
*Assistant Examiner* — Mohammed S Adam
(74) *Attorney, Agent, or Firm* — CANTOR COLBURN LLP

(57) ABSTRACT

The present invention relates to a needle channel usable in a hair transplant device, and the needle channel can be coupled to the outer circumferential surface of a central shaft inside the hair transplant device so as to be slidable in a vertical direction, and comprises: a body part having a tubular inner space; a needle coupled to the lower end of the body part; a core shaft slidably arranged in the tubular inner space and inside the needle; a slot longitudinally formed in the body part, and opened radially and outwardly from the central axis of the central shaft; a lever coupled to the upper end of the core shaft, and arranged to be slidable in a vertical direction in the slot.

11 Claims, 30 Drawing Sheets

(56) References Cited

U.S. PATENT DOCUMENTS

| | | | | |
|---|---|---|---|---|
| 6,110,189 A | * | 8/2000 | Markman | A61B 17/3468 606/187 |
| 2014/0243870 A1 | * | 8/2014 | Wesley | A61B 90/50 606/187 |
| 2018/0132892 A1 | | 5/2018 | Oostman, Jr. | |

FOREIGN PATENT DOCUMENTS

| | | | |
|---|---|---|---|
| KR | 1020160142683 A | 12/2016 | |
| KR | 1020170110357 A | 10/2017 | |
| KR | 10-2018-0001376 A | 1/2018 | |
| KR | 101862387 B1 | 5/2018 | |
| WO | 2016/042579 A2 | 3/2016 | |

OTHER PUBLICATIONS

International Search Report dated Sep. 3, 2019 for PCT/KR2019/006203, citing the above reference(s).

* cited by examiner

NEEDLE CHANNEL USED FOR HAIR TRANSPLANTER AND NEEDLE CHANNEL BUNDLE HAVING THE NEEDLE CHANNELS

CROSS-REFERENCE TO RELATED PATENT APPLICATION

This application claims priority from Korean Patent Application No. 10-2018-0076789, filed on Jul. 2, 2018 in the Korean Intellectual Property Office, the disclosure of which is incorporated herein by reference in its entirety.

BACKGROUND

1. Field

The present disclosure relates to a hair transplanter, and more particularly, to a bundle type hair transplanter having a plurality of hair transplantation needles mounted therein in a bundle type.

2. Description of the Related Art

A hair transplanter is a medical device that is used for a hair therapy procedure for transplanting hair by harvesting hair follicles from a hair growth area of a scalp and implanting the hair follicles into a bald scalp (balding patient).

A related-art hair transplanter includes a needle (transplantation needle) and a core shaft slidably inserted into the needle, and a bundle type hair transplanter having a plurality of needle channels mounted therein and each including a needle and a core shaft as one unit has been developed to transplant more hair.

However, such a bundle type hair transplanter has numerous driving motors and a complicated structure to operate the needle channels. That is, the bundle type hair transplanter should have at least three motors to perform an operation of rotating the needle channels to transplant hair, an operation of pushing one needle channel into the scalp, and an operation of returning the core shaft inside the needle, independently, and should have a complicated device structure to implement these operations.

SUMMARY

Embodiments of the present disclosure provide a hair transplanter which includes a needle channel bundle having more needle channels mounted therein than in a related-art hair transplanter by attaching the plurality of needle channels to an outer circumference of a rotary body.

Embodiments of the present disclosure also provide a hair transplanter which performs an operation of returning a core shaft by using a mechanical structure, rather than a separate driving device, such that a component cost and a device complexity can be reduced in comparison to a related-art hair transplanter.

Embodiments of the present disclosure also provide a hair transplanter which performs operations of rotating needle channels, ejecting a needle channel, and returning with only a mechanical device without a driving motor.

According to an embodiment, there is provided a needle channel usable in a hair transplanter, the needle channel being configured to be coupled to an outer circumference of a center shaft in the hair transplanter to be slidable up and down, the needle channel including: a body having a tubular inner space formed therein; a needle coupled to a lower end of the body; a core shaft slidably disposed in the tubular inner space and the needle; a slot formed on the body in a longitudinal direction and opened in an outward radial direction from a center axis of the center shaft; a lever coupled to an upper end of the core shaft, and disposed to be slidable up and down in the slot; and a spring fitted over a circumference of the core shaft and having an upper end supported on the lever and a lower end supported on a bottom surface of the slot.

According to an embodiment, there is provided a needle channel bundle provided with a plurality of needle channels usable in a hair transplanter, the needle channel bundle including: a center shaft disposed in the hair transplanter in a longitudinal direction; and a plurality of needle channels, wherein the plurality of needle channels are arranged on an outer circumference of the center shaft at equal intervals in a radial direction with reference to a center axis of the center shaft, and are coupled to the center shaft to be slidable up and down.

According to an embodiment, the needle channel bundle is formed by attaching the plurality of needle channels to the outer circumference of a rotary body radially, such that more needle channels can be mounted in comparison to a related-art hair transplanter.

According to an embodiment, the core shaft can be returned by a mechanical structure, and no separate driving means is required to return the core shaft, and accordingly, there are effects that a complexity of a device structure can be reduced and a component cost can be reduced.

In addition, according to an embodiment, there is provided a hair transplanter which can perform the operations of rotating, ejecting, and returning a needle channel only by a mechanical device without a driving motor.

BRIEF DESCRIPTION OF THE DRAWINGS

The above and other features and advantages will become more apparent by describing in detail exemplary embodiments with reference to the attached drawings in which.

DETAILED DESCRIPTION OF EXEMPLARY EMBODIMENTS

Figure 1:
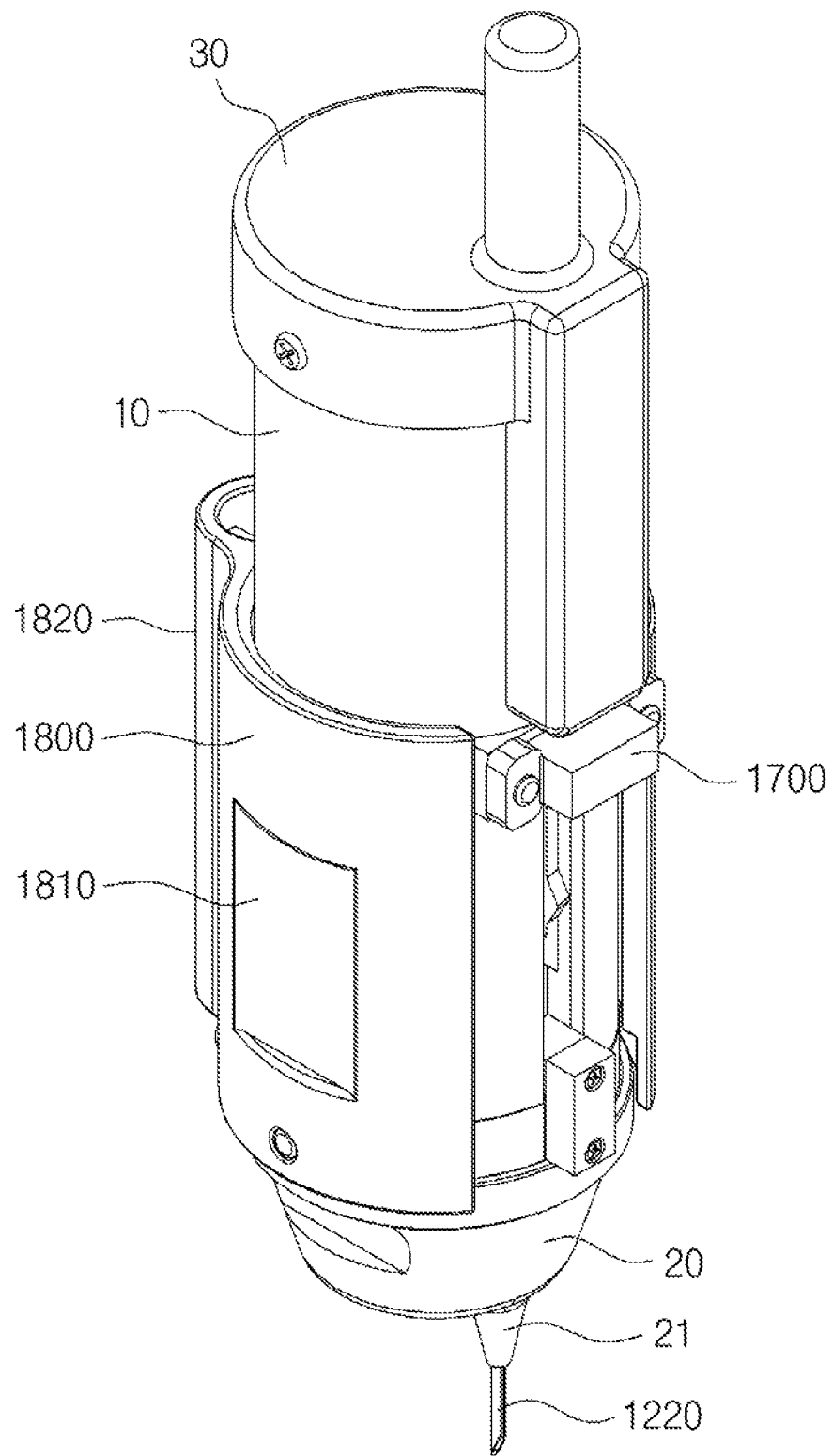
FIG. 1 is a perspective view of a hair transplanter according to a first embodiment of the present disclosure.

Exemplary embodiments will now be described more fully with reference to the accompanying drawings to clarify aspects, other aspects, features and advantages of the inventive concept. The exemplary embodiments may, however, be embodied in many different forms and should not be construed as limited to the exemplary embodiments set forth herein. Rather, the exemplary embodiments are provided so that this disclosure will be thorough and complete, and will fully convey the scope of the application to those of ordinary skill in the art.

It will be understood that when an element is referred to as being "on" (or "under", "on the right of", or "on the left of") another element, the element can be directly on (or "under", "on the right of", or "on the left of") another element or intervening elements. In the drawings, length or thickness of elements are exaggerated for easy understanding of technical features.

The expressions such as "upper", "lower", "left", "right", "front", "rear", etc. used in the specification to explain a position relationship between elements do not mean a directions or location as an absolute criterion, and are relative expressions used for convenience of explanation with reference to a corresponding drawing when the present disclosure is explained with reference to each drawing.

If the terms such as 'first' and 'second' are used to describe elements, these elements should not be limited by such terms. These terms are used for the purpose of distinguishing one element from another element only. The exemplary embodiments include their complementary embodiments.

As used herein, the singular forms are intended to include the plural forms as well, unless the context clearly indicates otherwise. It will be further understood that the terms "comprise" and/or "comprising," when used in this specification, do not preclude the presence or addition of one or more other components.

Hereinafter, exemplary embodiments will be described in greater detail with reference to the accompanying drawings. The matters defined in the description, such as detailed construction and elements, are provided to assist in a comprehensive understanding of the exemplary embodiments. However, it is apparent that the exemplary embodiments can be carried out by those of ordinary skill in the art without those specifically defined matters. In the description of the exemplary embodiment, certain detailed explanations of related art are omitted when it is deemed that they may unnecessarily obscure the essence of the inventive concept.

Hair Transplanter of First Embodiment

Figure 2:
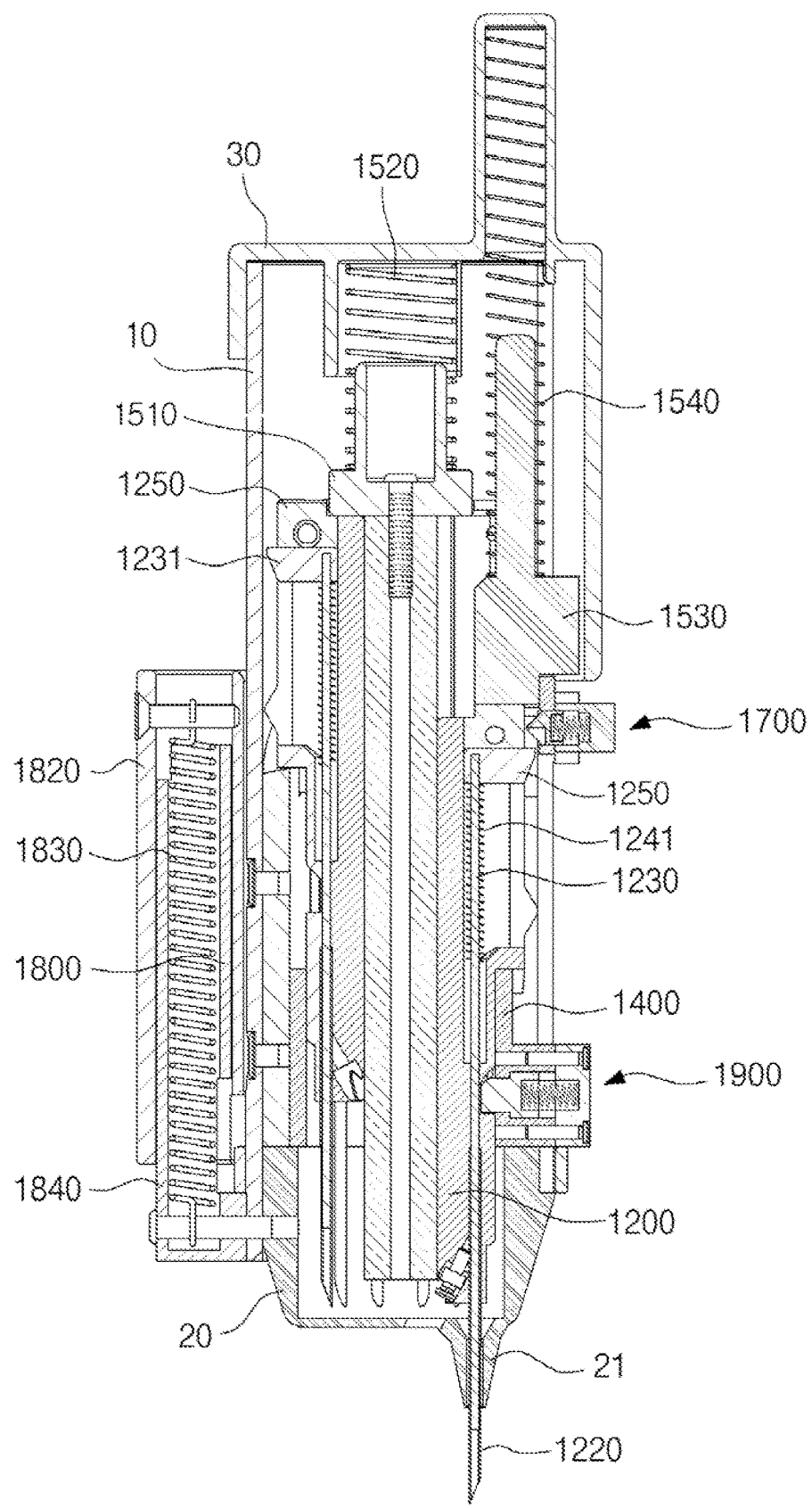
FIG. 2 is a cross-sectional view of the hair transplanter according to an embodiment.
Figure 3:
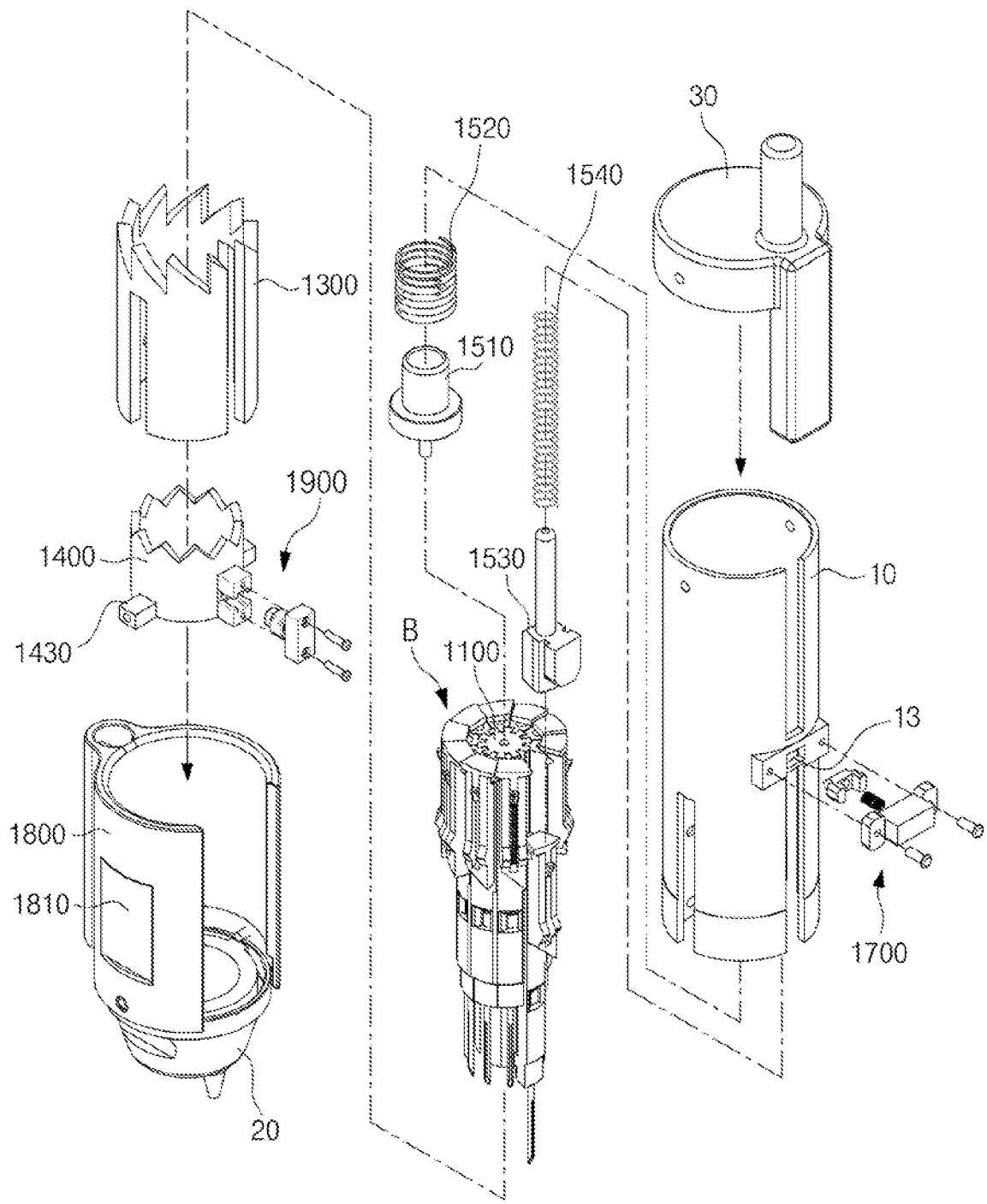
FIG. 3 is an exploded perspective view of the hair transplanter according to an embodiment.

FIG. 1 is a perspective view of a hair transplanter according to a first embodiment, FIG. 2 is a cross-sectional view of the hair transplanter, and FIG. 3 is an exploded perspective view.

Referring to the drawings, the hair transplanter according to the first embodiment includes a case 10, and a lower cap 20 and an upper cap 30 coupled to a lower portion and an upper portion of the case 10, respectively.

A needle channel bundle in which a plurality of needle channels 1200 are coupled in the form of a bundle is rotatably disposed inside the case 10. The needle channel bundle may include a center shaft 1100 and the plurality of needle channels 1200 radially arranged on the outer circumference of the shaft 1100 at equal intervals.

A channel rotation unit is disposed around the outer circumference of the needle channel bundle to rotate the needle channel bundle by a predetermined angle corresponding to one channel. In the illustrated embodiment, the channel rotation unit may include a cylindrical elevation gear holder 1400 which surrounds the outer circumference of the needle channel bundle, and a cylindrical ratchet support holder 1300 which surrounds the outer circumference of the elevation gear holder 1400.

The ratchet support holder 1300 is attached and fixed to the inside of the case 10. The elevation gear holder 1400 may slide up and down. In an embodiment, every time the elevation gear holder 1400 ascends and descends a single time, the needle channel bundle may be rotated by the predetermined angle. For example, the needle channel bundle may be rotated as much as one needle channel by a single ascending/descending operation of the elevation gear holder 1400. A detailed configuration and an operation of the channel rotation unit will be described in detail below with reference to FIGS. 12 to 15F.

A core shaft locking portion 1700 is disposed on a side surface of the case 10. The core shaft locking portion 1700 has a function of temporarily stopping a movement of the core shaft by locking the core shaft 1230 (see FIGS. 5A and 5B), which is slidably disposed in the needle channel 1200.

The lower cap 20 is attachably and detachably coupled to the lower end of the case 10 to cover the lower end of the case 10. The lower cap 20 has a nozzle 21 formed on a lower surface thereof to allow a single needle channel 1200 to pass therethrough, such that the single needle channel 1200 protrudes downward by a predetermined distance through the nozzle 21.

The hair transplanter includes a push bar 1530 to push down a single needle channel of the needle channel bundle. The push bar 1530 is disposed between the upper portion of the needle channel bundle and the upper cap 30 in the case 10. When the push bar 1530 pushes down the needle channel 1200, the pushed needle channel 1200 protrudes by a predetermined distance through the nozzle 21.

Figure 4:
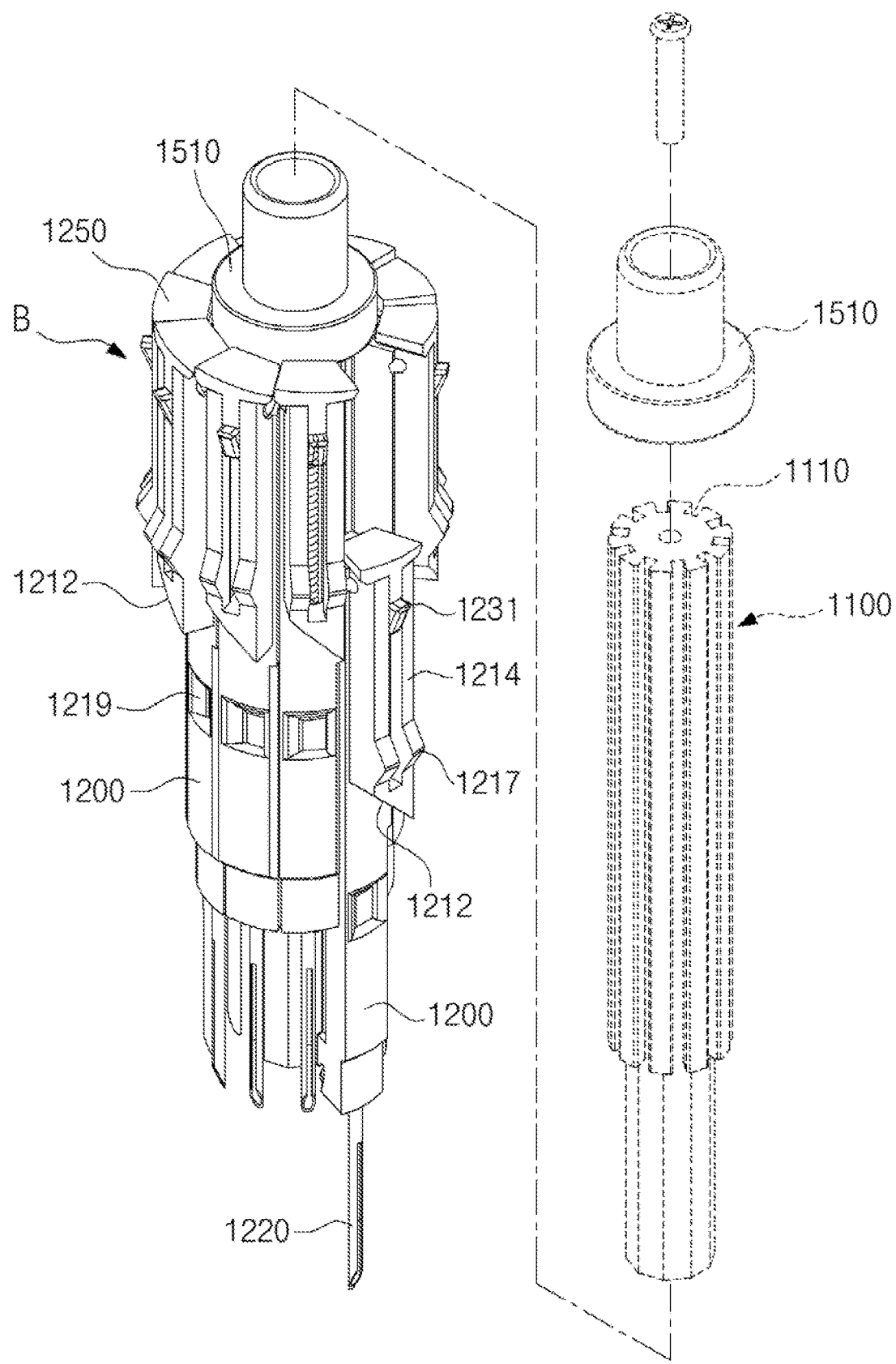
FIG. 4 is a view to illustrate a needle channel bundle according to an embodiment.

FIG. 4 is a view to illustrate the needle channel bundle according to an embodiment. Referring to the drawing, the needle channel bundle B includes the center shaft 1100 and the plurality of needle channels 1200 coupled to the outer circumference of the center shaft 1100 to be slidable up and down.

A plurality of slide rails 1110 are formed on the outer circumference of the center shaft 1100 radially at equal intervals with reference to a center axis of the center shaft 1100. In an embodiment, the slide rails 1110 are recessed lengthways in the vertical direction.

A head member 1510 having a larger diameter than that of the center shaft 1100 is fixed to the upper end of the center shaft 1100 by means of a bolt to prevent the needle channels 1200 from being moved up further. The head member 1510 may be integrally formed with the center shaft 1100 or may be separately formed and coupled to the center shaft 1100.

A spring 1520 is interposed between the head member 1510 and the upper cap 30, and elastically supports the needle channel bundle B downward.

Figure 5A:
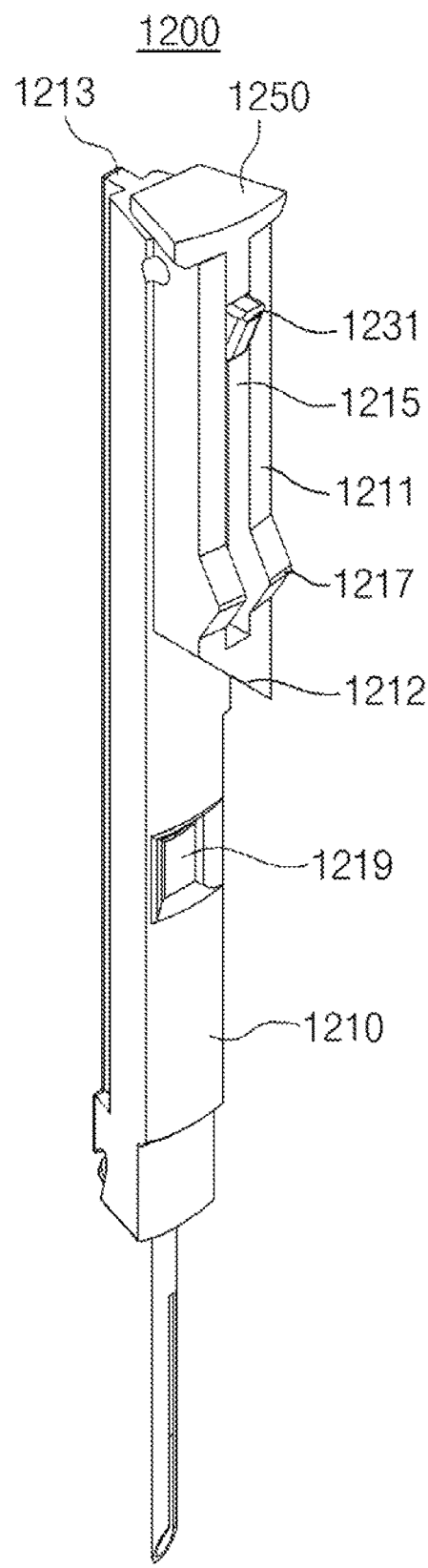
FIGS. 5A and 5B are a perspective view and a cross-sectional view of the needle channel according to an embodiment.
Figure 5B:
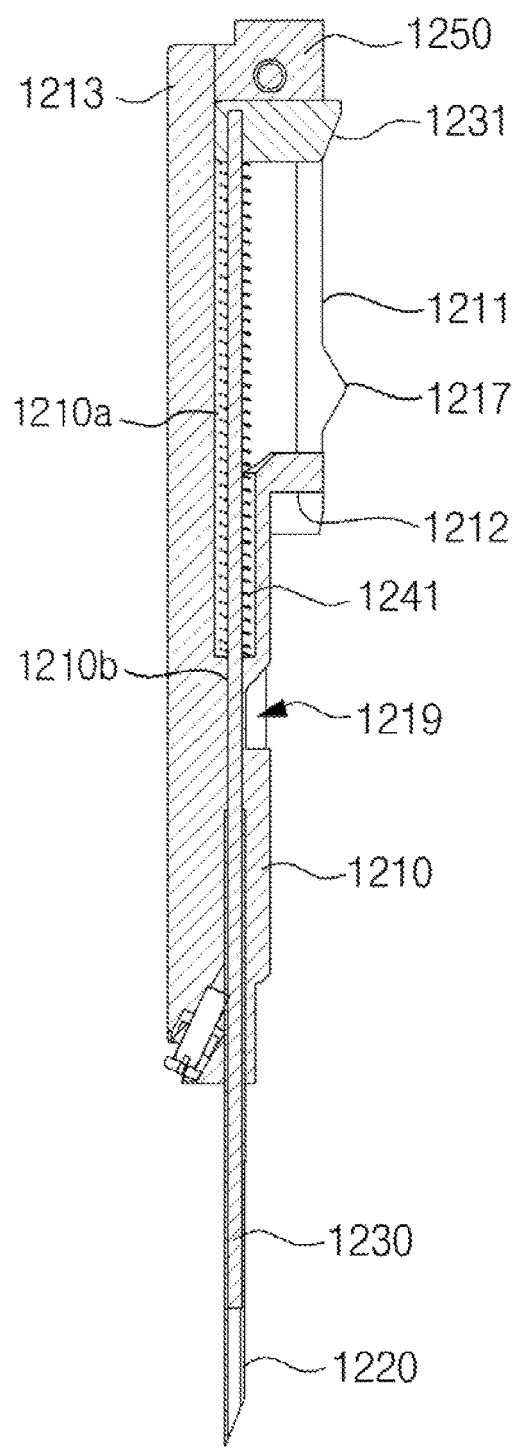
Figure 6:
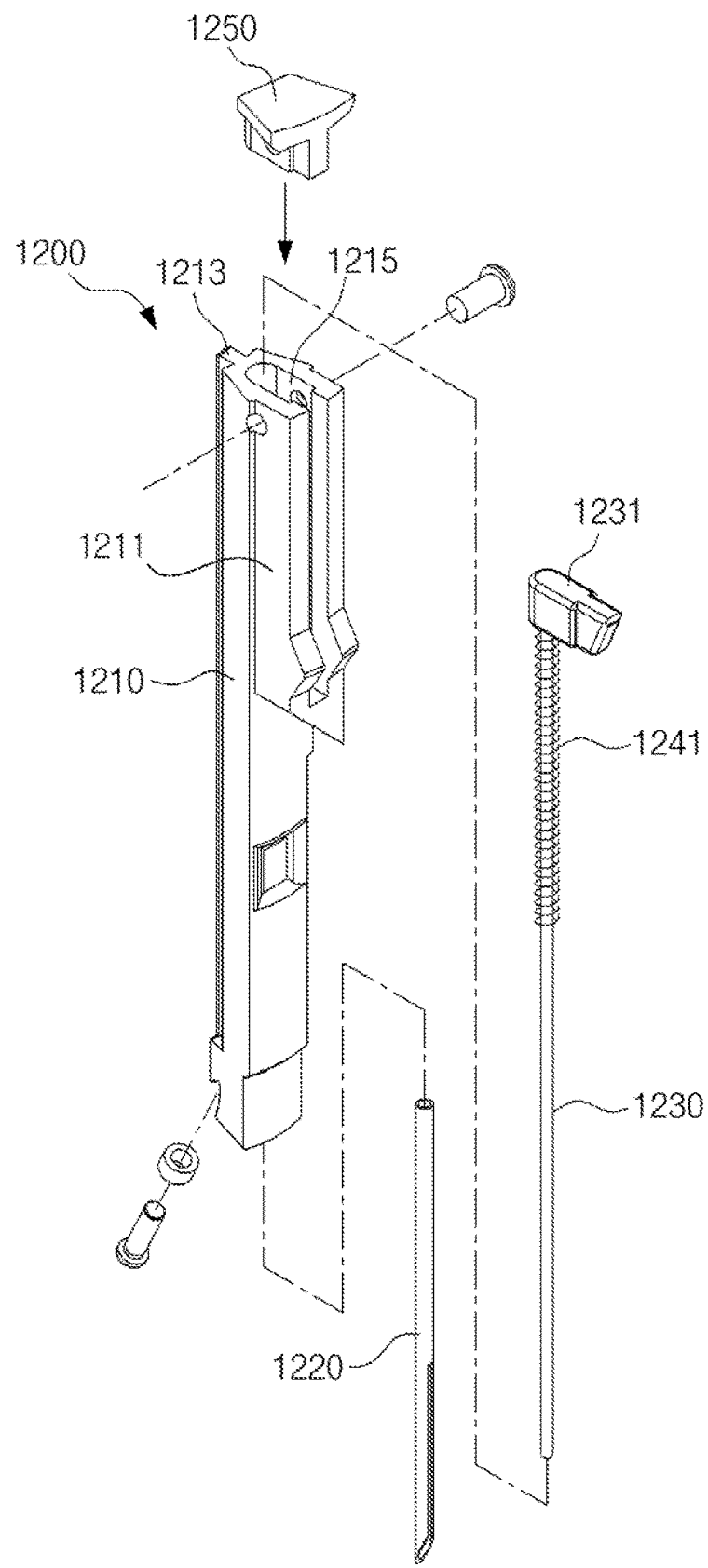
FIG. 6 is an exploded perspective view of the needle channel according to an embodiment.

FIGS. 5A to 6 are views illustrating the needle channel 1200 according to an embodiment. Specifically, FIG. 5A is a perspective view of the needle channel 1200 and FIG. 5B is a cross-sectional view, and FIG. 6 is an exploded perspective view.

Referring to the drawings, the needle channel 1200 may include a body 1210 having a tubular inner space, a needle 1220 coupled to a lower portion of the body 1210, and the core shaft 1230 slidably disposed in the tubular inner space.

The tubular inner space of the body 1210 may include a first diameter portion 1210a formed on an upper portion and having a relatively large diameter, and a second diameter portion 1210b formed on a lower portion and having a relatively small diameter. The lower second diameter portion 1210b has a diameter enough to allow the core shaft 1230 to pass therethrough, and the upper first diameter portion 1210a has a diameter enough to receive a spring 1241 fitted over the circumference of the core shaft 1230. The needle 1220 for hair transplantation is inserted into and coupled to the body 1210 through an opened lower end of the second diameter portion 1210b of the body 1210.

Figures 7A, 7B:
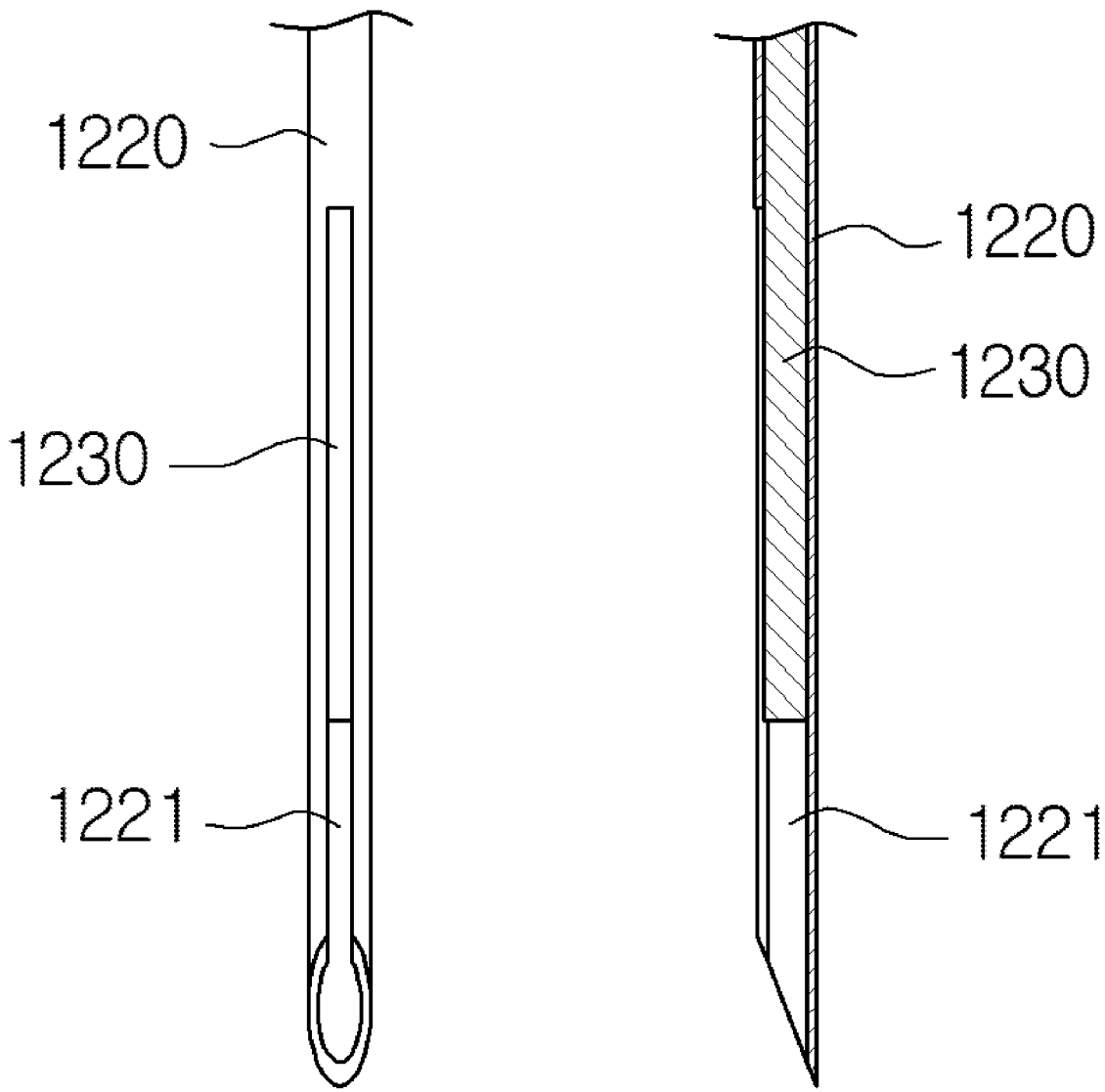
FIGS. 7A and 7B are views to illustrate a lower structure of a needle and a core shaft according to an embodiment.

FIGS. 7A and 7B are views illustrating a structure of a lower end of the needle 1220 according to an embodiment. FIG. 7A illustrates the needle as viewed from the radial outside of the needle channel bundle B toward the center shaft, and FIG. 7B is a cross-sectional view as viewed from the side.

As can be seen from the drawings, a slot hole 1221 is formed on a side surface of the lower end of the needle 1220, and is opened to the outside to easily thread a hair follicle. The core shaft 1230 is inserted into the inner space of the needle 1220, and is arranged to have a lower end thereof positioned under the uppermost end of the slot hole 1221 and not to protrude over the lowermost end of the needle 1220. The slot hole 1221 is formed to face in an outward radial direction of the needle channel bundle B, thereby providing convenience to an operator in transplanting hair follicles.

The body 1210 includes a side surface protrusion 1213 formed along one side surface thereof lengthwise in the vertical direction. The side surface protrusion 1213 protrudes toward the center shaft 1100, that is, in an inward radial direction, and has a protruding shape to be engaged with the recess portion of the slide rail 1110 of the center shaft 1100. Accordingly, the side surface protrusion 1213 of the body 1210 is inserted into and engaged with the slid rail 1110 of the center shaft 1100, such that the needle channel 1200 can slide up and down along the slid rail 1110.

Figure 8A:
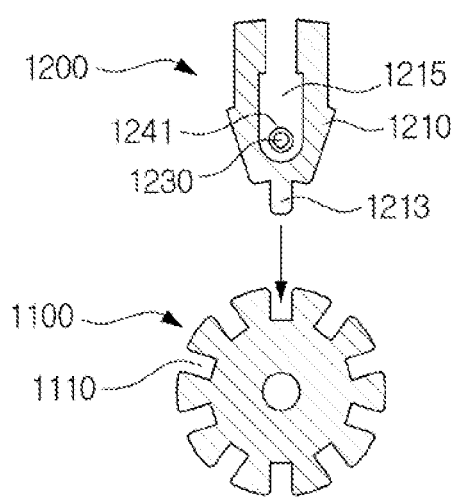
FIGS. 8A and 8B are views to illustrate a structure in which a plurality of needle channels are coupled to a center shaft according to an embodiment.
Figure 8B:
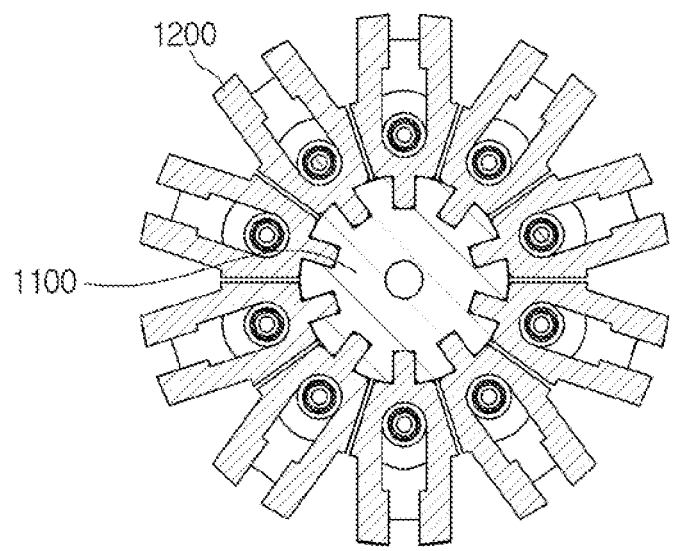

Regarding this, FIG. 8 schematically illustrates a cross section of the needle channel bundle B taken at a substantially middle height. The slide rails 1110 are formed along the outer circumference of the center shaft 1100, and the side surface protrusion 1213 of the needle channel 1220 is inserted into each of the slide rails 1110, such that the needle channels 1200 are radially arranged along the entire outer circumference of the center shaft 1100 at equal intervals, and are coupled to the center shaft 1100.

According to the embodiment of the present disclosure described above, since the needle channels 1200 are attached to the outer circumference of the center shaft 1100 rather than to the inside, more needle channels than in a related-art hair transplanter can be attached. That is, the related-art hair transplanter has a center shaft formed similar to a cylindrical magazine of a revolver, and has a needle channel inserted into the inner space of the center shaft. However, the needle channels are attached along the outer circumference of the center shaft according to the embodiment of the present disclosure. Therefore, if the diameter of the case 10 is the same as the diameter of a case of the related-art hair transplanter, more needle channels can be coupled in the same space in comparison to the related-art hair transplanter.

Referring back to FIGS. 5A to 6, the needle channel 1200 includes a locking protrusion 1211 formed opposite the side surface protrusion 1213 of the body 1210, that is, extending from the body 1210 in the outward radial direction of the needle channel bundle B. The locking protrusion 1211 includes a slot 1215 formed in the vertical direction, a projection 1217 extending from the surface of the locking protrusion 1211 to further protrude in the outward radial direction, and a saw-toothed ratchet gear tooth 1212 formed at the lower end of the locking protrusion 1211 and having an inclination angle only in one direction.

The slot 1215 is formed vertically on the surface of the locking protrusion 1211 facing in the outward radial direction, and fluidly communicates with the tubular inner space of the body 1210. The core shaft 1230 is disposed in the tubular inner space, and a lever 1231 is coupled to an upper end of the core shaft 1230. The lever 1231 may be guided by the slot 1215 and may slide up and down. The spring 1241 is fitted over the circumference of the core shaft 1230. The upper end of the spring 1241 is supported on the lower surface of the lever 1231, and the lower end of the spring 1241 is supported on a stepped portion between the first diameter portion 1210a and the second diameter portion 1210b of the body 1210.

Figure 9A:
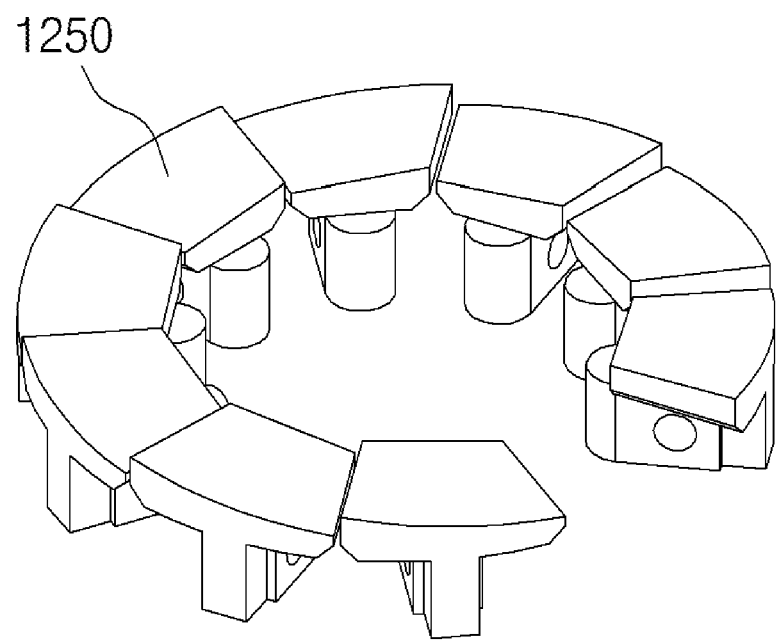
FIGS. 9A and 9B are views to illustrate an upper cover coupled to an upper portion of the needle channel.
Figure 9B:
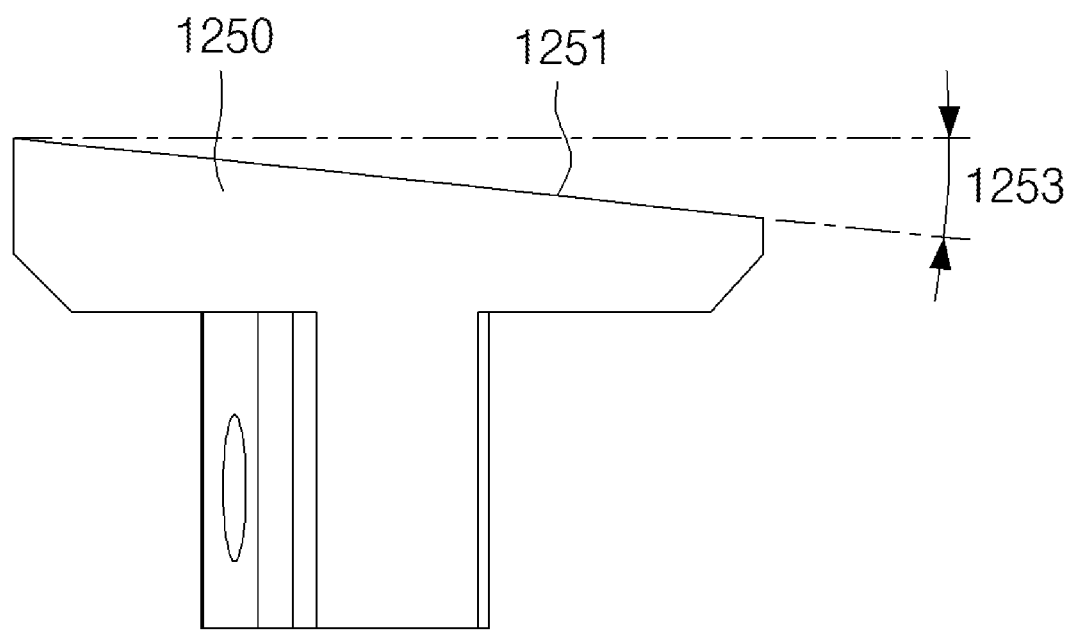

The upper end of the slot 1215 is opened and an upper cover 1250 is inserted into and coupled to the opened upper end of the slot 1215. The upper cover 1250 serves as a stopper to prevent the lever 1231 from being moved up further. As shown in FIGS. 9A and 9B, the upper surface of the upper cover 1250 inclines in one direction so as to allow the needle channel bundle B to smoothly rotate. That is, the surface 1251 of the upper cover 1250 inclines by a predetermined inclination angle 1253 in the rotation direction of the needle channel bundle, thereby preventing the push bar 1530 contacting the upper surface of the upper cover 1250 from interfering with the rotation of the needle channel bundle B.

The body 1210 of the needle channel 1200 may further include a locking recess 1219. The locking recess 1219 is formed on the surface of the body 1210 facing in the outward radial direction, under the locking protrusion 1211. The locking recess 1219 may receive a latch 1910 of a needle channel locking portion 1900. A detailed shape and a function of the locking recess 1219 will be described below with reference to FIGS. 13A to 14.

As shown in FIGS. 2 and 3, the hair transplanter includes the push bar 1530 to push down a single needle channel 1200 of the needle channel bundle. The push bar 1530 is elastically coupled to the upper cap 30 through an elastic member such as a spring 1540, and is disposed to press down a single needle channel 1200 of the needle channel bundle B. The push bar 1530 and the nozzle 21 are aligned in the same vertical line, and accordingly, when the push bar 1530 pushes down the needle channel 1200, the pushed needle channel 1200 may protrude by a predetermined distance through the nozzle 21.

Figure 10A:
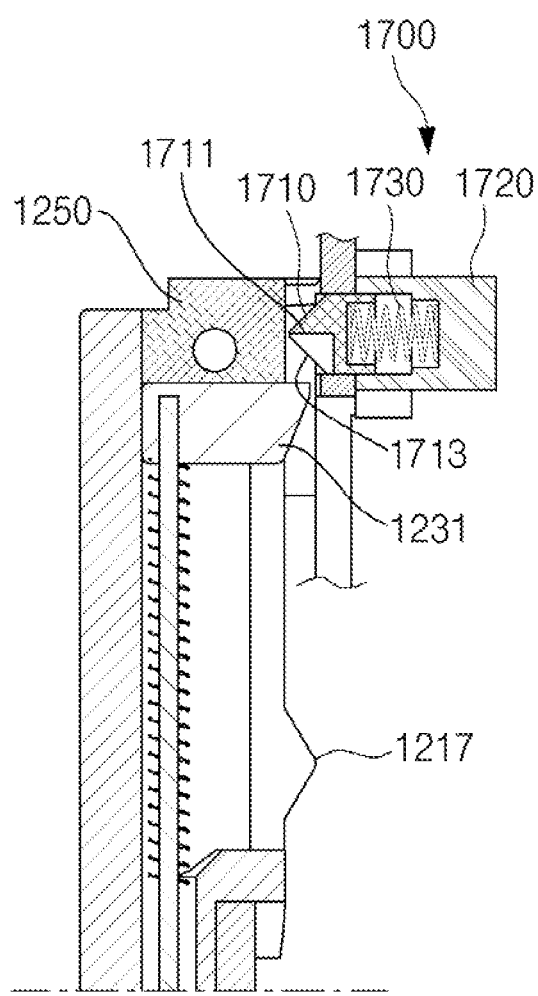
FIGS. 10A and 10B are views to illustrating a core shaft locking portion according to an embodiment.
Figure 10B:
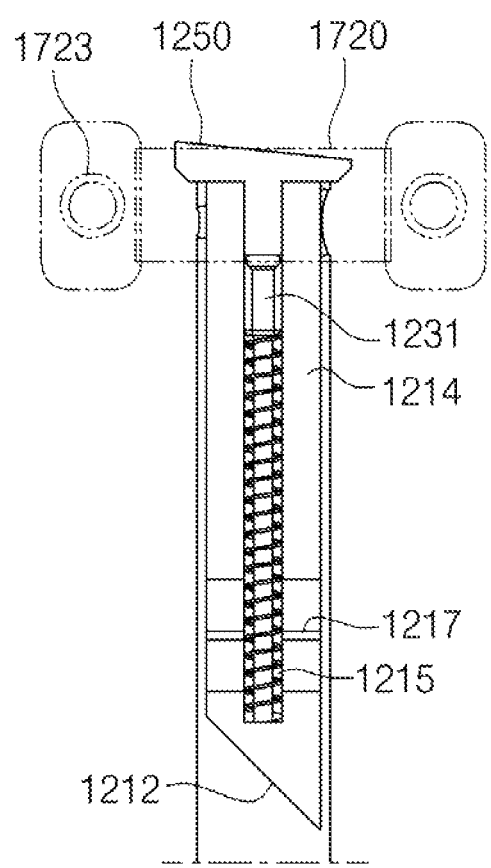

FIGS. 10A and 10B illustrate a core shaft locking portion 1700 according to an embodiment. The core shaft locking portion 1700 is disposed on a radially outward surface of the needle channel pushed down by the push bar 1530. In the illustrated embodiment, the core shaft locking portion 1700 is disposed on one side surface of the case 10. The core shaft locking portion 1700 functions to temporarily stop the movement of the core shaft 120 in the needle channel 1200 while the needle channel 1200 is moving up after being pushed down by the push bar 1530.

Referring to the drawings, the core shaft locking portion 1700 may include a latch 1710, a latch receiving portion 1720 for receiving the latch 1710, and an elastic member 1730 interposed between the latch 1710 and the latch receiving portion 1720.

The latch 1710 is disposed within a distance to be able to interfere with a vertical movement of the lever 1231, and is configured to elastically retract in the outward radial direction of the needle channel bundle B.

The latch receiving portion 1720 may be coupled and fixed to one side surface of the case 10 by means of bolts through bolt holes 1723 of extension regions formed on left and right sides thereof. The bolt holes 1723 of the latch receiving portion 1720 may be formed in a rectangular shape to make the position of the latch 1710 adjustable. The position of the latch determines the length of the core shaft 1230 protruding from the nozzle 21 in a hair follicle implantation operation, and influences a depth of a transplanted hair follicle. The latch receiving portion 1720 has a space to receive the latch 1710 therein, and the elastic member 1730 such as a spring is interposed in this space. Accordingly, the latch 1710 is disposed within a distance to interfere with the vertical movement of the lever 1231, and is configured to elastically retract in the outward radial direction of the needle channel bundle B.

When a force is not applied to the latch 1710, the latch 1710 protrudes from the latch receiving portion 1720 (in the inward radial direction of the needle channel bundle B), and comes into contact with the lever 1231 when the lever 1231 slides up and down. In this case, as shown in FIG. 10A, an upper portion of a contact surface of the latch 1710 coming into contact with the lever 1231 inclines upward, and a lower lever contact surface 1711 is substantially horizontal. Accordingly, when the lever 1232 moves down from above the latch 1710, the lever 1231 may move down while pushing the latch 1710 toward the latch receiving portion 1720. However, when the lever 1231 moves up from under the latch 1710, an upper surface of the lever 1231 comes into contact with the lever contact surface 1711 of the latch 1710 and is caught, and thus the lever 1232 does not move up further.

The projection 1217 protrudes from the side surfaces of the slot 1215 of the needle channel 1200 in the outward radial direction of the needle channel bundle B. The projection 1217 may protrude to the same level as the lever 1231 or may further protrude than the lever 1231 in the outward radial direction. In addition, a horizontal width of the latch 1710 may be set to interfere with not only the vertical movement of the lever 1231 but also the vertical movement of the projection 1217, and, as shown in FIGS. 11A to 11D, the upper portion of the contact surface of the latch 1710 coming into contact with the projection 1217 may incline upward, and a lower projection contact surface 1713 may incline downward. Accordingly, the projection 1217 may move up and/down while pushing the latch 1710 toward the latch receiving portion 1720 in any case of a case where the needle channel 1200 moves up from under the latch 1710 and a case where the needle channel 1200 moves down from above the latch 1710.

The operation of locking and unlocking the core shaft 1230 by the core shaft locking portion 1700 having the above-described configuration will be described with reference to FIGS. 11A to 11D.

Figure 11A:
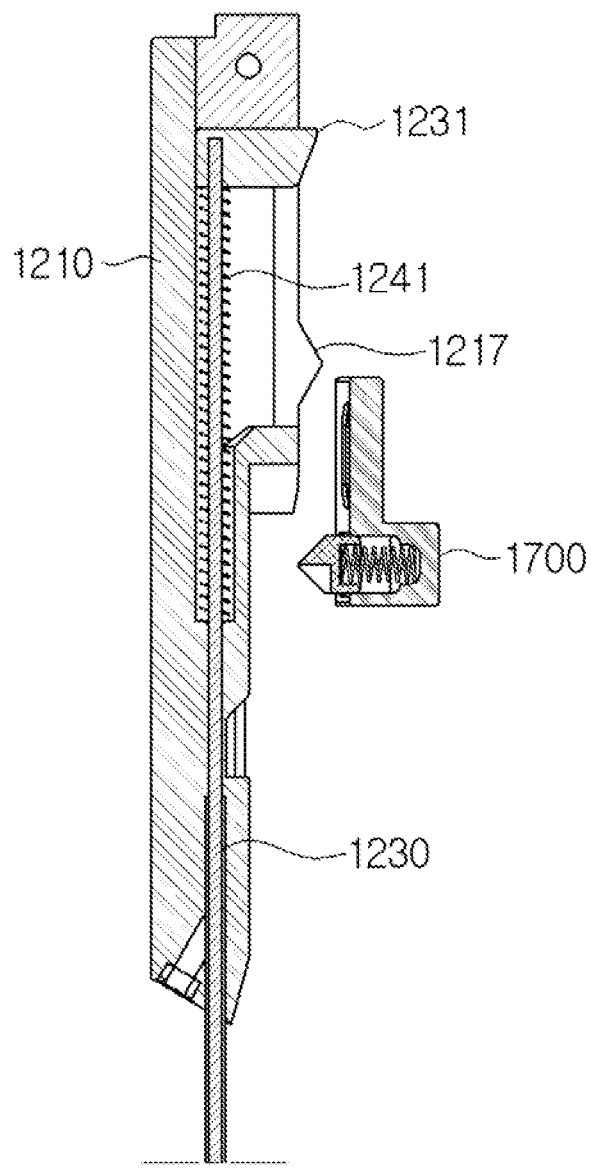
FIGS. 11A to 11D are views to illustrate operations of locking and unlocking the core shaft according to an embodiment.

FIG. 11A illustrates a state before the needle channel 1200 attached to the needle channel bundle B moves down. In this state, the lever 1231 and the projection 1217 of the needle channel 1200 are all positioned above the latch 1710 of the core shaft locking portion 1700.

When the push bar 1530 pushes down the needle channel 1200, the needle channel 1200 moves down. When the needle channel 1200 moves down, the projection 1217 and the lever 1231 come into contact with the inclined surface of the latch 1710, and thus the needle channel 1200 and the lever 1231 move down while pushing the latch 1710 toward the latch receiving portion 1720.

Figure 11B:
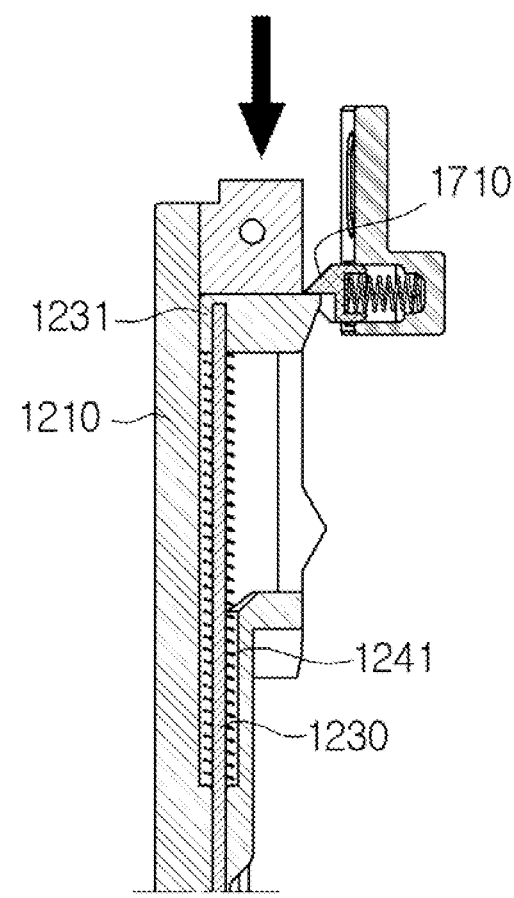

Thereafter, when the lever 1231 moves down further under the latch 1710 as shown in FIG. 11B, the upper surface of the lever 1231 comes into contact with the lever contact surface 1711 of the latch 1710, and the lever 1231 is locked by the latch 1710.

Figure 11C:
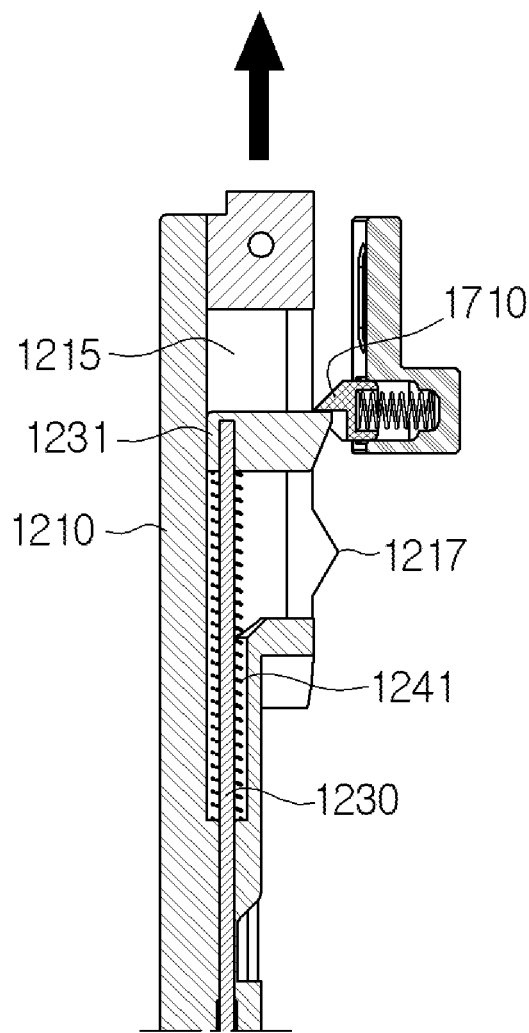
Figure 11D:
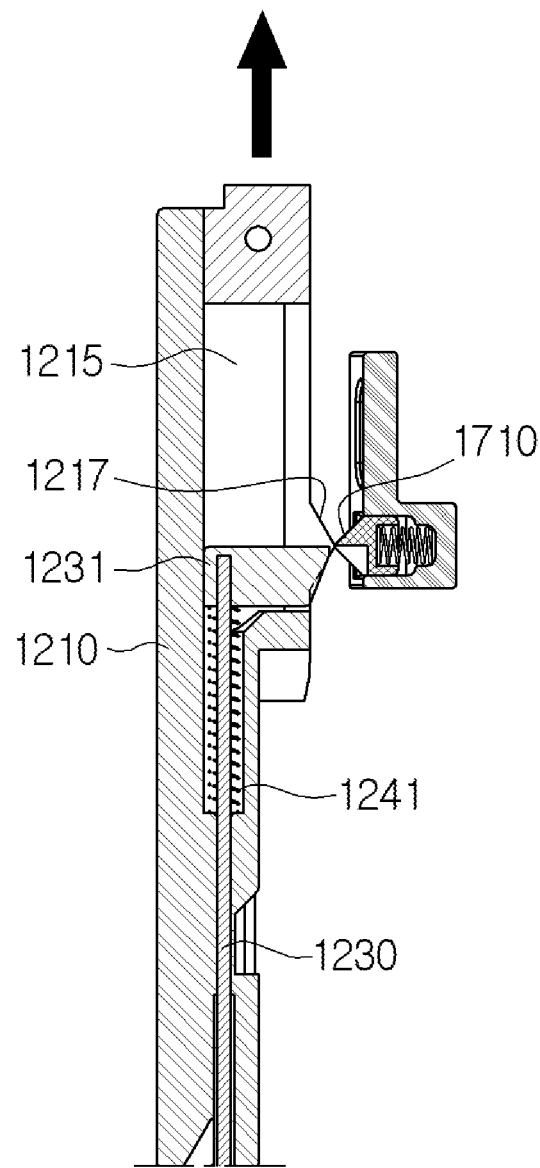

Accordingly, when the needle channel 1200 moves up as shown in FIG. 11C, the lever 1231 and the core shaft 1230 integrally coupled therewith do not move up since the lever 1231 is locked by the latch 1710.

Thereafter, when the needle channel 1200 moves up further, the projection 1217 come into contact with the latch 1710 and pushes the latch 1710 toward the latch receiving portion 1720. Accordingly, the latch 1710 retracts into the latch receiving portion 1720, such that the lever 1231 is unlocked, and the lever 1231 and the core shaft 1230 move up due to elasticity of the spring 1241 and return to the state shown in FIG. 11A.

According to the embodiment described above, the core shaft 1230 can return by a new mechanical structure. The related-art hair transplanter requires a separate driving unit such as a driving motor to return the core shaft 1230, but a driving motor for returning the core shaft 1230 is not required in the present disclosure. Therefore, technical effects of reducing a component cost and a device complexity can be achieved in comparison with the related-art hair transplanter.

Figure 12:
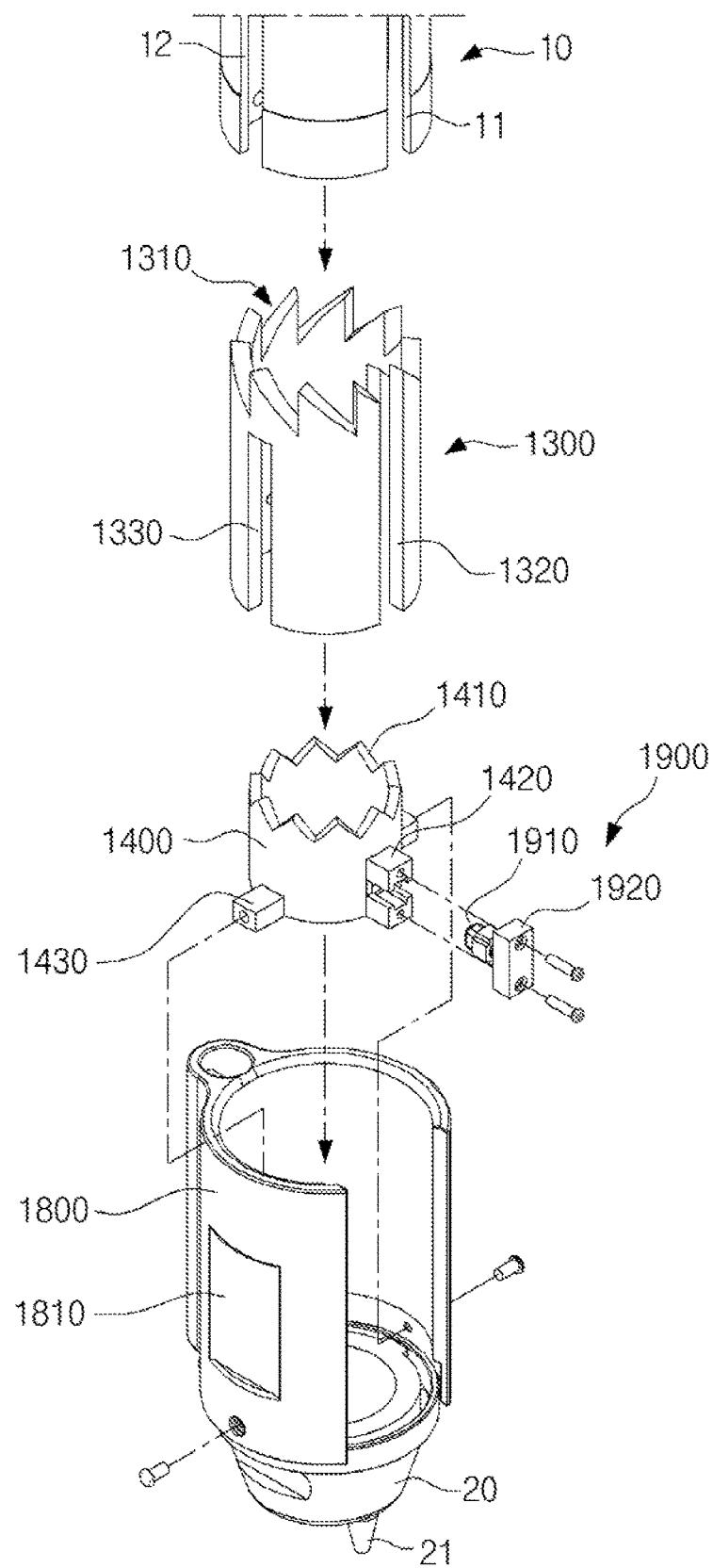
FIG. 12 is an exploded perspective view to illustrate some elements of the hair transplanter according to an embodiment.

Hereinafter, the channel rotation unit for rotating the needle channel bundle will be described. Referring to FIGS. 2, 3, and 12, the hair transplanter according to an embodiment includes the cylindrical elevation gear holder 1400 surrounding the outer circumference of the needle channel bundle, and the cylindrical ratchet support holder 1300 surrounding the outer circumference of the elevation gear holder 1400.

The elevation gear holder 1400 is a substantially cylindrical member, and is arranged to surround the outer circumference of the needle channel bundle B. An upper end surface of the cylindrical elevation gear holder 1400 is formed to come into contact with a lower end surface of the locking protrusion 1211 of the needle channel 1200, that is, a lower surface of the ratchet gear tooth 1212. That is, sharp wedge-type protrusions 1410 are continuously formed on the upper surface of the elevation gear holder 1400, and the same number of wedge-type protrusions 1410 as the number of ratchet gear teeth 1212 are formed to be engaged with the ratchet gear teeth 1212 of the needle channel bundle.

The ratchet support holder 1300 is a substantially cylindrical member and is arranged to surround the needle channel bundle in contact with the outer circumference of the elevation gear holder 1400. The upper end surface of the ratchet support holder 1300 is configured to come into contact with the lower surface of the ratchet gear tooth 1212 of the locking protrusion portion 1211 of the needle channel 1200. That is, saw-toothed ratchet gear recesses 1310 each having an inclination angle in one direction are formed on the upper surface of the ratchet support holder 1300 to be engaged with the ratchet gear teeth 1212.

The ratchet support holder 1300 is attached and fixed to the inside of the case 10. On the other hand, the elevation gear holder 1400 is slidable up and down. In an embodiment, at least one connection protrusion piece 1430 is formed on an outer circumference of the elevation gear holder 1400, and for example, is coupled with a manual operation handle 1800.

The manual operation handle 1800 is formed to surround the outer circumference of the case 10 at least in part, and is arranged to be slidable up and down along the outer circumference of the case 10. That is, the elevation gear holder 1400 and the manual operation handle 1800 coupled thereto via the connection protrusion piece 1430 are integrally slidable up and down with respect to the case 10 and the ratchet support holder 1300 attached to the inside of the case 10. In this case, slots 12, 1330 are vertically formed on the case 10 and the ratchet support holder 1300, respectively, to allow the connection protrusion piece 1430 to penetrate therethrough and to prevent the case 10 and the ratchet support holder 1300 from interfering with the vertical movement of the connection protrusion piece 1430.

The needle channel locking portion 1900 is attached to a side surface of the elevation gear holder 1400. The needle channel locking portion 1900 locks a single needle channel 1200 pushed by the push bar 1530 and moving down, and lets the needle channel 1200 move according to a vertical movement of the elevation gear holder 1400.

Figure 13A:
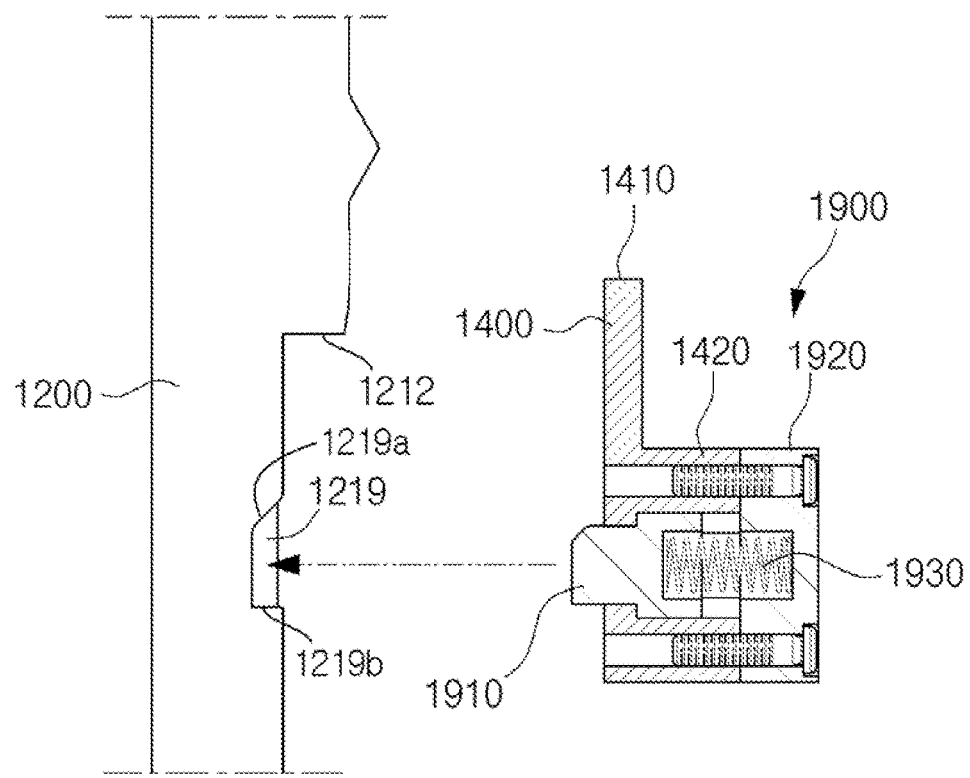
FIGS. 13A to 14 are views to illustrate a needle channel locking portion according to an embodiment.
Figure 13B:
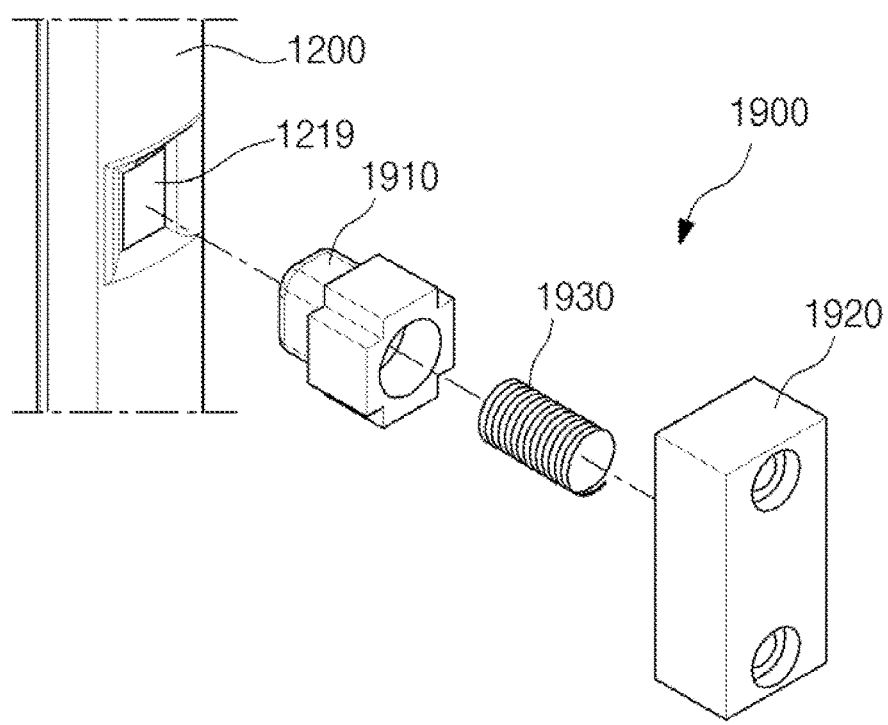
Figure 14:
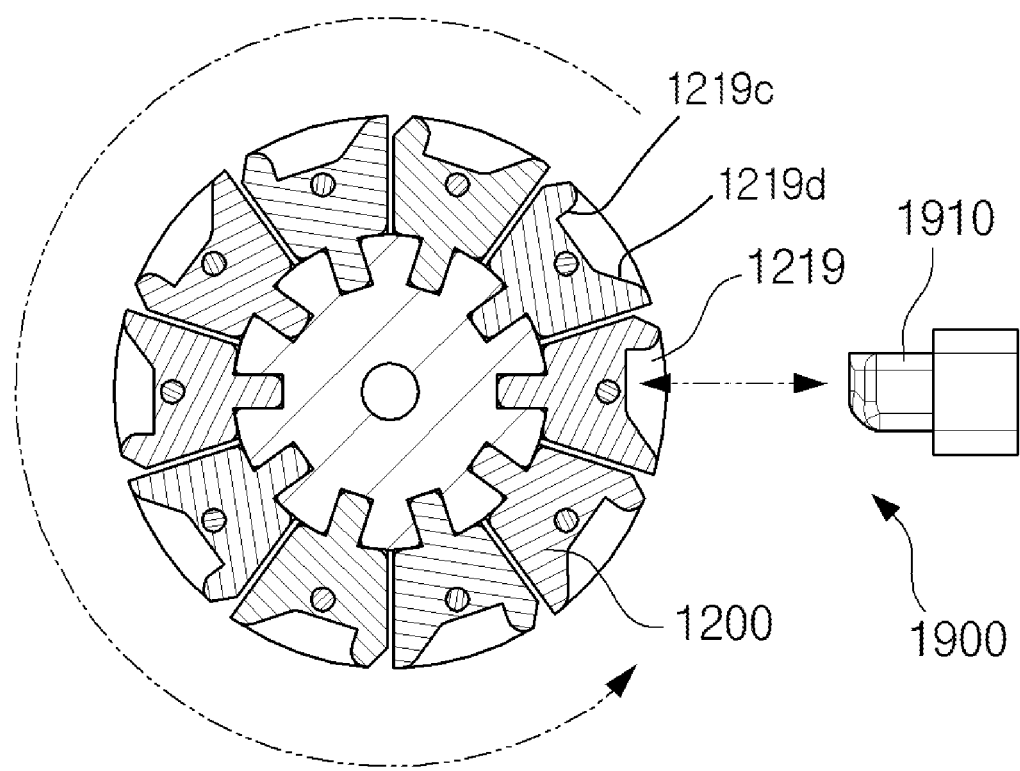

Referring to FIGS. 12 to 14, the needle channel locking portion 1900 may include a latch 1910, a latch receiving portion 1920 for receiving the latch 1910, and an elastic member 1930 interposed between the latch 1910 and the latch receiving portion 1920.

Connection protrusion pieces 1420 are formed on a certain side surface of the elevation gear holder 1400 to attach the needle channel locking portion 1900. Slots 11, 1320 are vertically formed on the case 10 and the ratchet support holder 1300, respectively, to allow the connection protrusion pieces 1420 to penetrate therethrough and to prevent the case 10 and the ratchet support holder 1300 from interfering with the connection protrusion pieces 1420 when the the elevation gear holder 1400 moves up and down.

The latch receiving portion 1920 may be coupled and fixed to the connection protrusion pieces 1420 by a coupling method such as coupling by a bolt. The latch receiving portion 1920 has a space to receive the latch 1910 therein, and the elastic member 1930 such as a spring is interposed in this space.

The latch 1910 is a cuboid member and may be engaged with the locking recess 1219 of the needle channel 1200. FIGS. 13A and 14 shows the needle channel locking portion 1900 as viewed from the left and above, respectively. As shown in FIGS. 13A and 14, from the viewpoint of the latch 1910, a right end surface 1219c and a lower end surface 1219b of the locking recess 1219 of the needle channel 1200 are formed at right angle to a surface plane of the body 1210, and a left end surface 1219d and an upper end surface 1219a are gently inclined surfaces by being chamfered. In addition, four edges of a protruding end of the latch 1910 corresponding to and coming into contact with the end surfaces of the locking recess 1219 may be formed at right angle or may be inclined surface by being chamfered. That is, from the viewpoint of the latch receiving portion 1920, an edge on a side of the rotation direction of the needle channel bundle B (the right edge in the illustrated embodiment) from among the four edges of the protruding end of the latch 1910, and the lower edge are formed at right angle, and an edge on a side of the opposite direction of the rotation of the needle channel bundle B (the left edge in the illustrated embodiment) and the upper edge are inclined surfaces by being chamfered. In an alternative embodiment, the right end surface 1219c of the locking recess 1219 and the right edge of the latch 1910 corresponding thereto may be formed at right angle or may be inclined surfaces.

When the latch 1910 is inserted and locked into the locking recess 1219, the needle channel 1200 moves according to a vertical movement of the elevation gear holder 1400. However, in this locking state, when the needle channel bundle is rotated in the counter clockwise direction as shown in FIG. 14, the latch 1910 retracts into the latch receiving portion 1920 and the needle channel 1200 is unlocked, and, when the needle channel bundle is rotated by a degree corresponding to one channel, the latch 1910 locks another needle channel 1200 (adjacent in the clockwise direction in FIG. 14).

As shown in FIG. 14, an edge 1219e of the body 1210 that is adjacent to the right end surface 1219c out of the two end surfaces of the locking recess 1219 of the body 1210 of each needle channel 1200 may be formed by being chamfered and rounded. Accordingly, when the needle channel bundle is rotated by one channel, the latch 1910 can be smoothly rotated without being interrupted or hindered by the edge of the body 1210 of the needle channel.

Therefore, according to the needle channel locking portion 1900 according to the present disclosure, every time the needle channel bundle is rotated by one channel, the operation of locking and unlocking one needle channel is automatically performed, and the needle channel locked by the latch 1910 moves according to the vertical movement of the elevation gear holder 1400. In addition, when a user presses down the handle to insert a needle into a scalp, the needle can be prevented from retracting into the nozzle.

Referring now to FIGS. 15A to 15F, an operation of rotating the needle channel by the channel rotation unit will be described. FIGS. 15A to 15F illustrate only parts of the ratchet support holder 1300 and the elevation gear holder 1400 and the ratchet gear teeth 1212 of two adjacent needle channels 1200 for convenience of explanation.

Figure 15A:
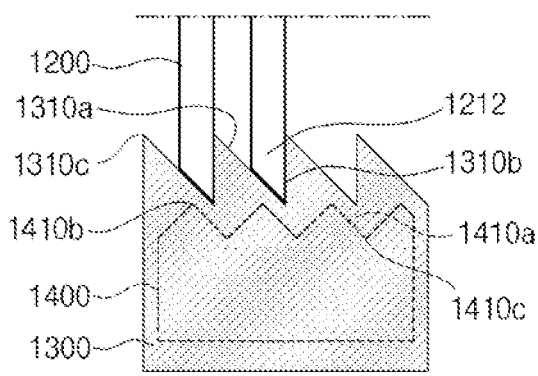
FIGS. 15A to 15F are views to illustrate an operation of rotating the needle channel according to an embodiment.

In FIG. 15A, when an external force is not applied to the elevation gear holder 1400 by the user, the elevation gear holder 1400 is positioned lower than the ratchet support holder 1300 due to the presence of a spring 1830, and the rachet gear teeth 1212 of the needle channel bundle are seated on and supported by the ratchet gear recesses 1310 of the ratchet support holder 1300 due to the presence of the spring 1520. In this case, one needle channel 1200 pushed down by the push bar 1530 is locked by the needle channel locking portion 1900 and moves down although it is not illustrated in FIGS. 15A to 15F.

An uppermost end 1410*b* of each of the wedge-type protrusions 1410 of the elevation gear holder 1400 is positioned between uppermost ends 1310*c* of the ratchet gear recess 1310.

Figure 15B:
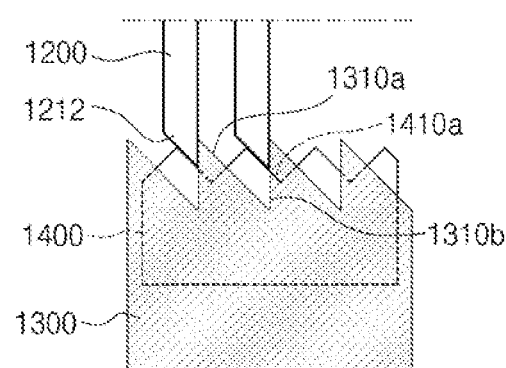
Figure 15C:
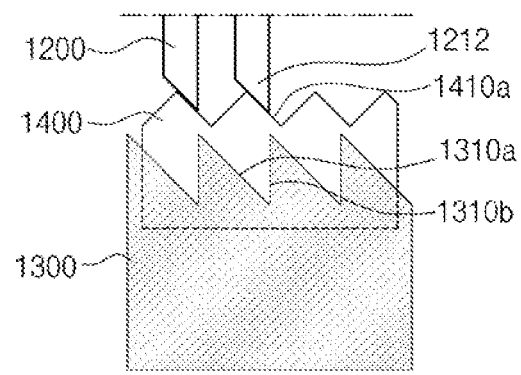

When the user raises the manual operation handle 1800, the elevation gear holder 1400 moves up along with the handle 1800. As the elevation gear holder 1400 gradually moves up, an inclined surface 1410*a* of the wedge-type protrusion 1410 of the elevation gear holder 1400 comes into contact with the ratchet gear tooth 1212 of the needle channel 1200, and the elevation gear holder 1400 moves up the entire needle channel bundle, as shown in FIGS. 15B and 15C. In this case, the needle channel bundle slides down along the inclined surfaces 1410*a* of the wedge-type protrusions 1410 due to the elasticity of the spring 1520, and is about to rotate. However, since the ratchet gear teeth 1212 are in contact with the inclined surfaces 1410*a* of the wedge-type protrusions 1410 and vertical surfaces 1310*b* of the ratchet gear recesses 1310 and are supported thereby, the needle channel bundle is not rotated and is moved up by the elevation gear holder 1400.

Figure 15D:
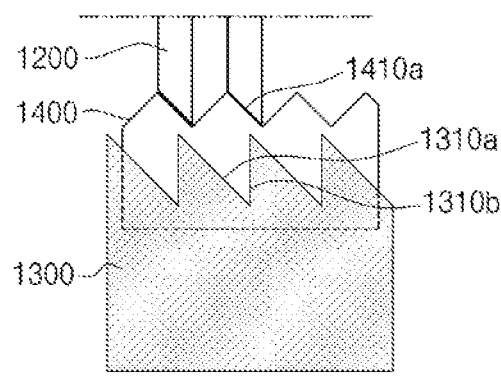

However, when the elevation gear holder 1400 moves up until the wedge-type protrusions 1410 are higher than the ratchet gear recesses 1310 (see FIG. 15C), the needle channel bundle is not supported by the vertical surfaces 1310*b* of the ratchet gear recesses 1310, and the ratchet gear teeth 1212 slide down along the inclined surfaces 1410*a* of the wedge-type protrusions 1410, and the needle channel bundle is rotated by a predetermined angle (FIG. 15D).

Figure 15E:
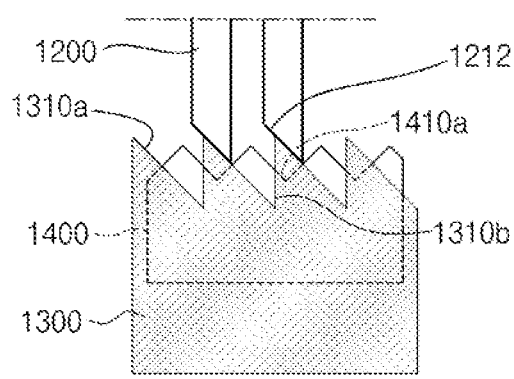
Figure 15F:
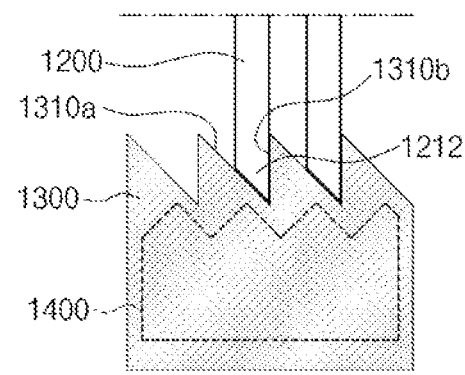

Thereafter, when the user releases the force of pushing up the handle 1800, the handle 1800 drops down due to the presence of the spring 1830, and also, the elevation gear holder 1400 moves down, such that the ratchet gear teeth 1212 of the needle channels 1200 come into contact with the inclined surfaces 1310*a* of the ratchet gear recesses 1310 (see FIG. 15E). When the wedge-type protrusions 1410 of the elevation gear holder 1400 move down under the ratchet gear recesses 1310 of the ratchet support holder 1300, the ratchet gear teeth 1212 slide down along the inclined surfaces 1310*a* of the ratchet gear recesses 1310, and the needle channel bundle is rotate again by a predetermined angle (FIG. 15F). Accordingly, comparing FIGS. 15A and 15F, it can be seen that the needle channel bundle is rotated by one channel.

According to the channel rotation unit according to an embodiment described above, every time the elevation gear holder 1400 is moved up and down a single time, the needle channel bundle is rotated by one channel, and a needle 1220 of a different channel is ejected through the nozzle 21 each time. Therefore, every time the user moves up and down the manual operation handle 1800 a single time, continuous hair transplantation can be performed while changing the needles 1220 one by one.

Figure 16:
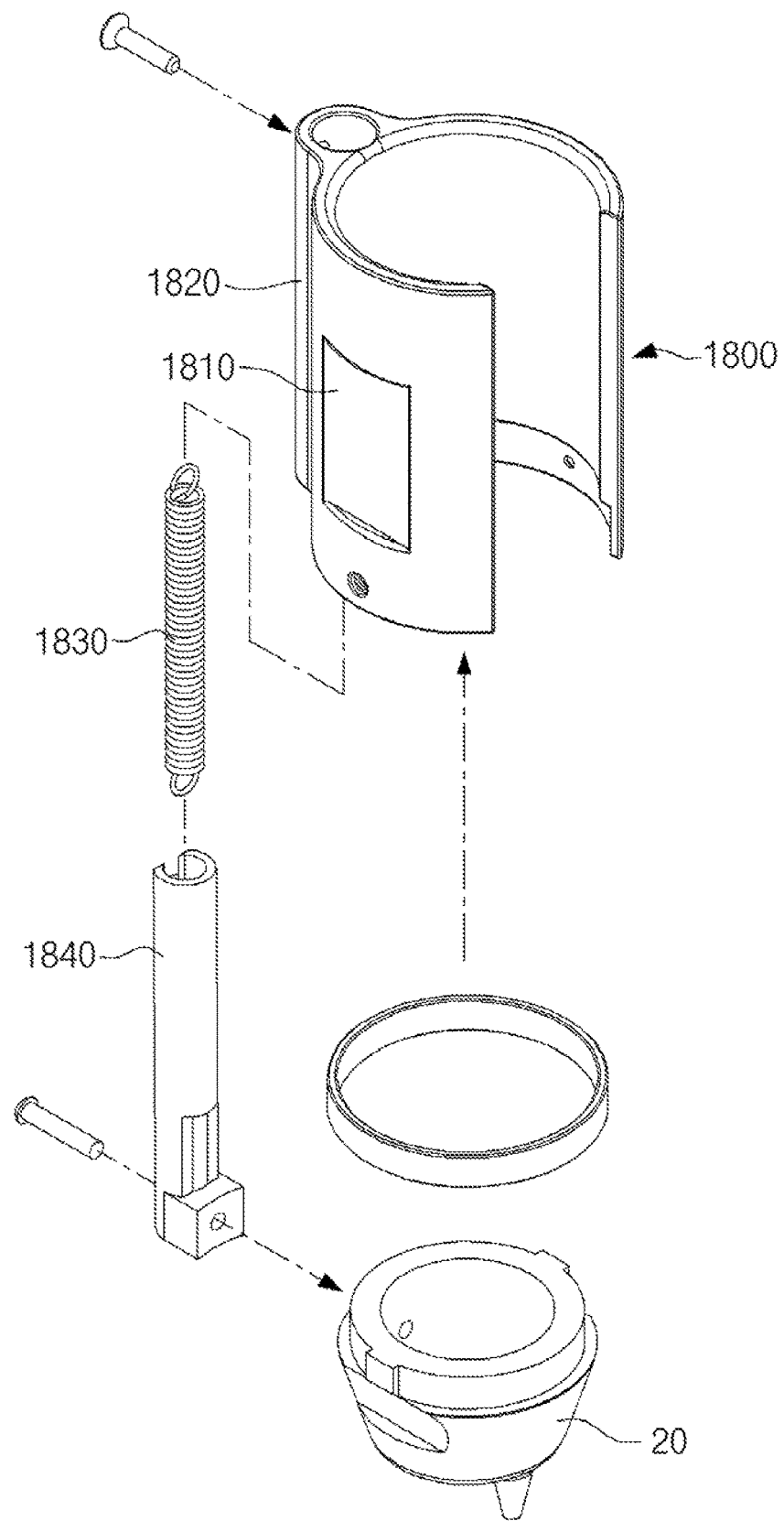
FIG. 16 is a view to illustrate a manual operation handle according to an embodiment.
Figure 17:
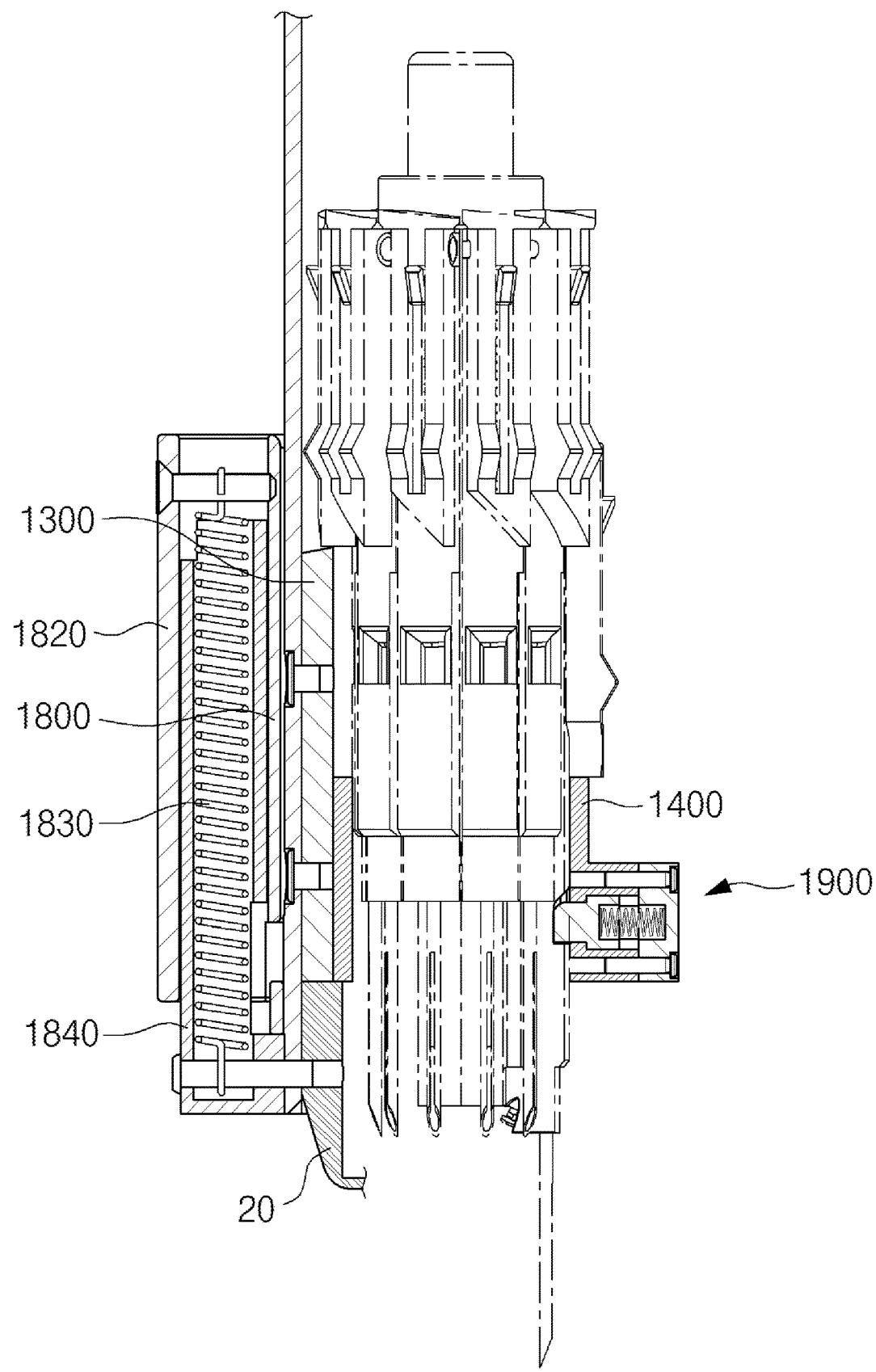
FIGS. 17 and 18 are cross-sectional views of one side and the other side of a portion of the hair transplanter having the manual operation handle mounted thereon according to an embodiment.
Figure 18:
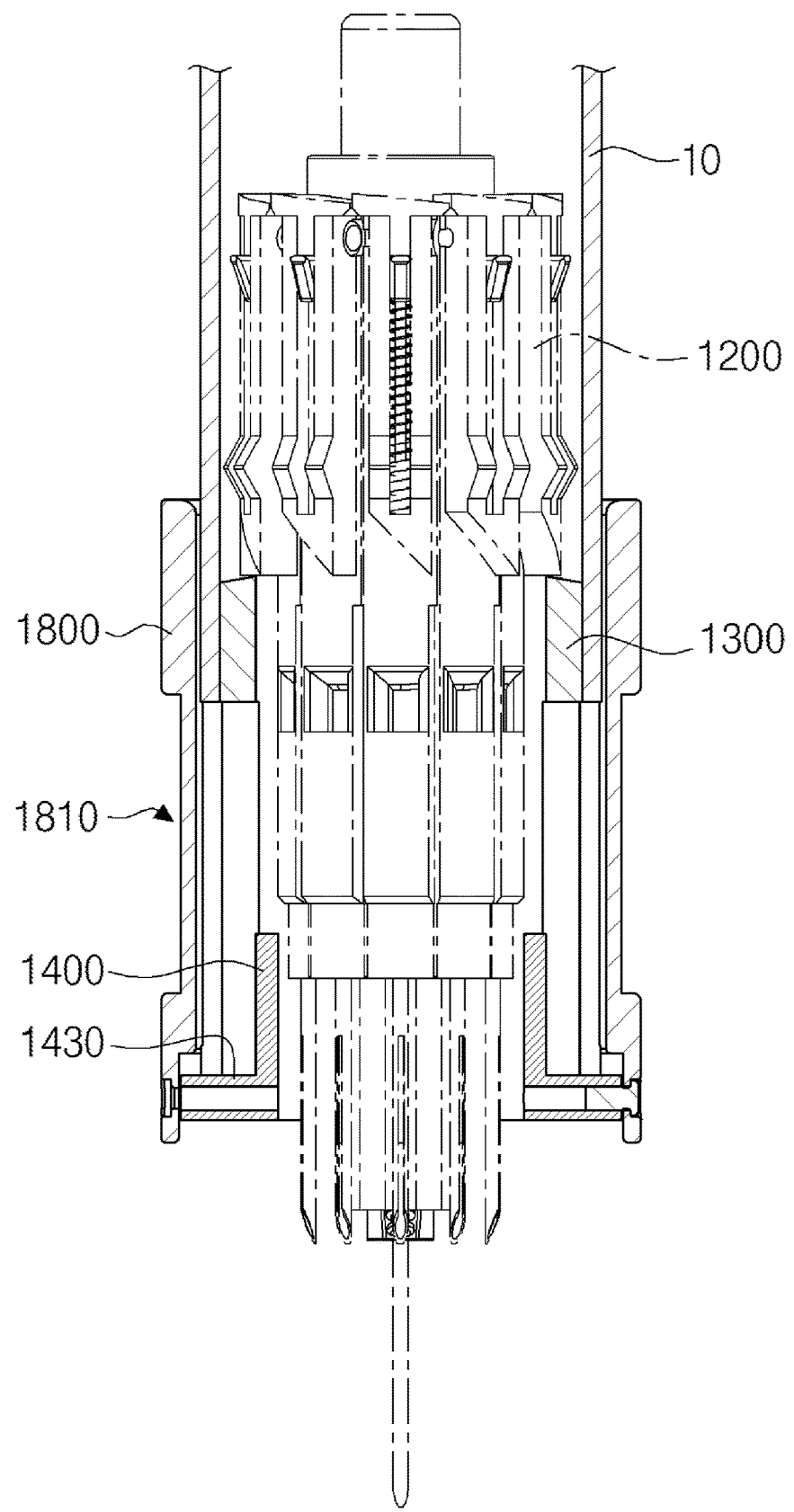

Hereinafter, the manual operation handle 1800 for moving up and down the elevation gear holder 1400 will be described with reference to FIGS. 16 to 18. FIG. 16 is a perspective view illustrating a coupling structure of the manual operation panel 1800 and the lower cap 20, and FIGS. 17 and 18 are cross-sectional views illustrating a part of the hair transplanter having the manual operation handle mounted thereon from different angles.

Referring to the drawings, the manual operation handle 1800 has a shape to surround the outer circumference of the case 10 at least in part. A handle recess 1810 may be recessed from a side surface of the handle 1800 to a predetermined depth to prevent a slip of a finger.

The handle 1800 may include a spring receiving portion 1820 formed on one side surface thereof to receive the spring 1830 in the vertical direction. The spring 1830 may be inserted into a spring lower coupling member 1840 surrounding the spring 1830 at least in part, and may be received in the spring receiving portion 1820. The spring 1830 may have an upper end fixed to an upper portion of the spring receiving portion 1820, and a lower end fixed to the spring lower coupling member 1840. In addition, the spring lower coupling member 1840 is coupled to the lower cap 20 or the case 10.

According to this configuration, when the user holds the manual operation handle 1800 and moves up the same, the spring 1840 stretches and an elastic force is applied. Therefore, when there is no external force, the manual operation handle 1800 moves down and returns to its original position due to the presence of the spring 1830.

Hair Transplanter of Second Embodiment

Hereinafter, a hair transpllanter according to a second embodiment will be described with reference to FIGS. 19 to 28.

Figure 19:
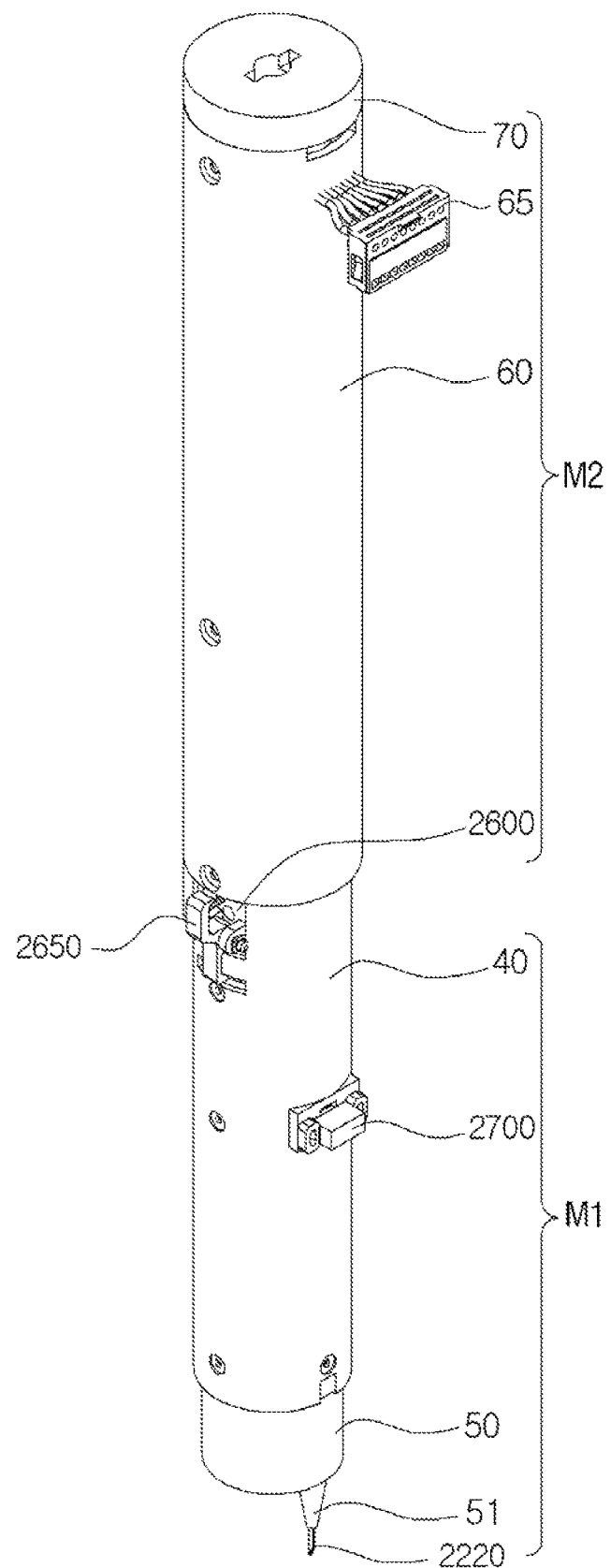
FIG. 19 is a perspective view of a hair transplanter according to a second embodiment of the present disclosure.
Figure 20:
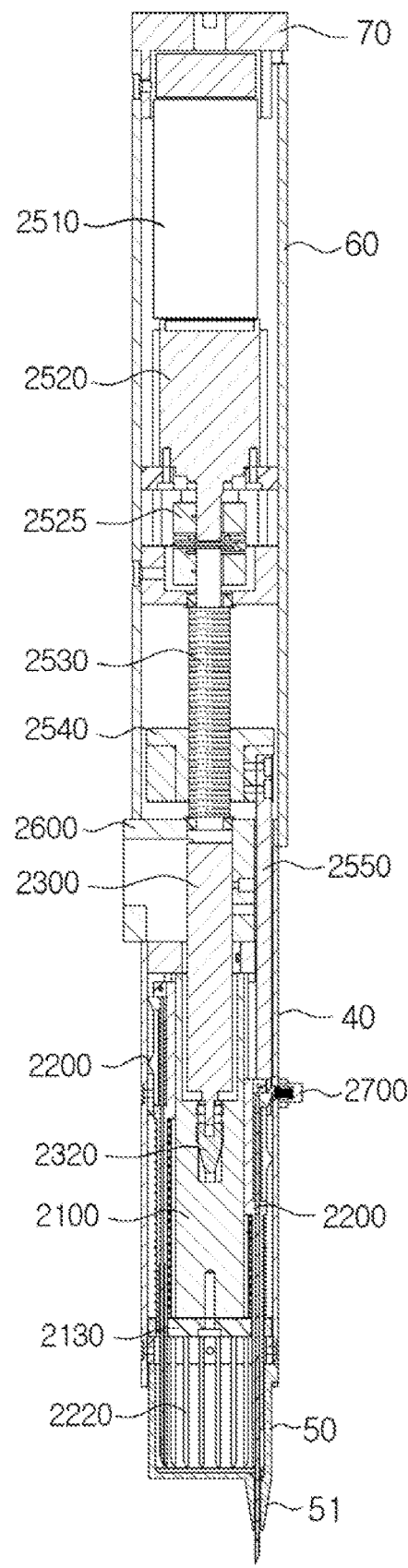
FIG. 20 is a cross-sectional view of the hair transplanter according to an embodiment.
Figure 21:
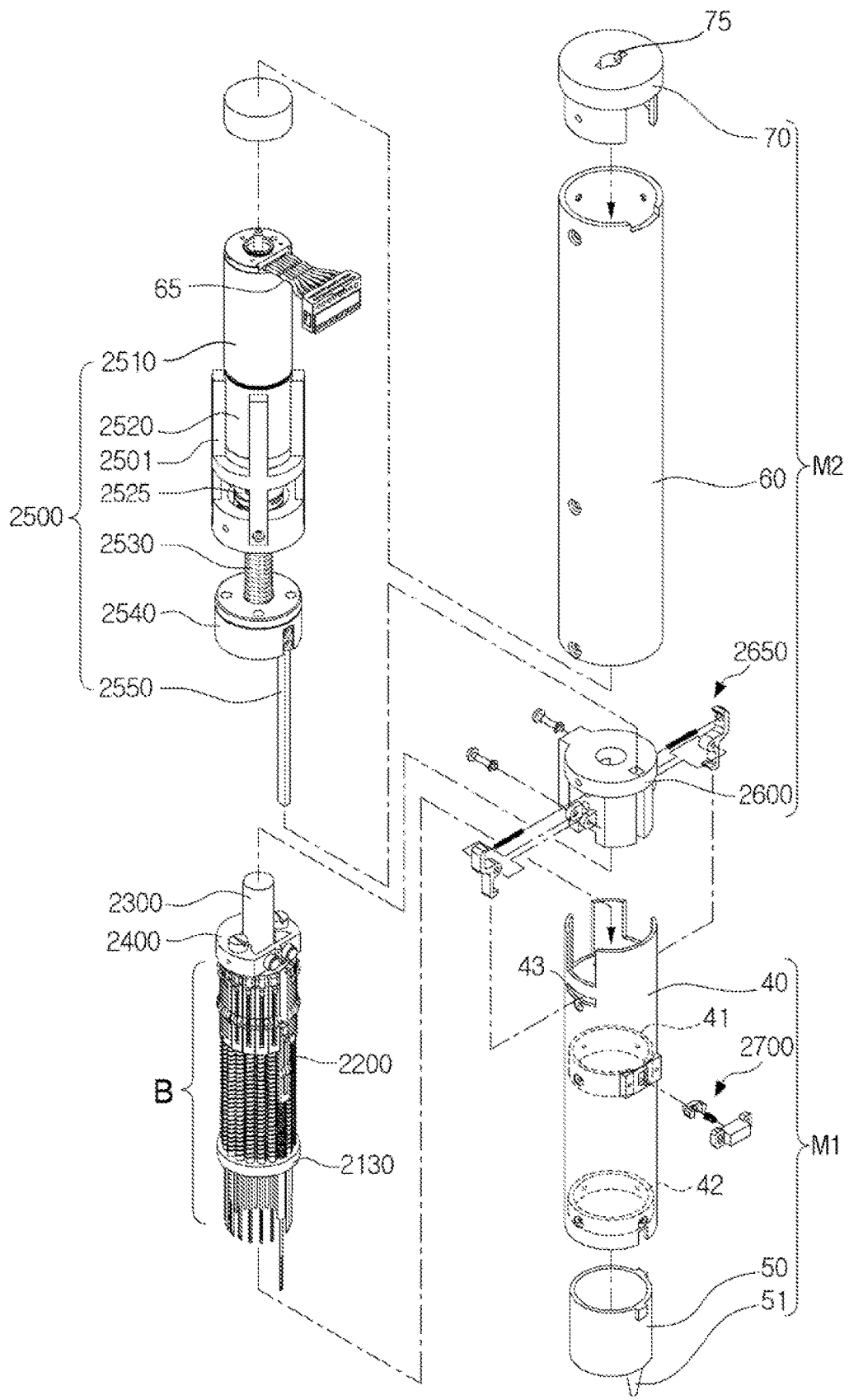
FIG. 21 is an exploded perspective view of the hair transplanter according to an embodiment.

FIG. 19 is a perspective view of the hair transplanter according to the second embodiment, FIG. 20 is a cross-sectional view of the hair transplanter, and FIG. 21 is an exploded perspective view.

Referring to FIGS. 19 to 21, the hair transplanter according to the second embodiment includes a lower module M1 and an upper module M2. The lower module M1 may be cased by a lower case 40 and a lower cap 50 coupled to a lower portion of the lower case 40, and the upper module M2 may be cased by an upper case 60, an upper cap 70 coupled to an upper portion of the upper case 60, and a bracket 2600 coupled to a lower portion of the upper case 60.

It is desirable that the lower module M1 and the upper module M2 are detachably coupled to each other, such that the lower module M1 after use can be replaced with a new lower module M1. In the illustrated embodiment, a lever type module coupling portion 2650 may be installed on the bracket 2600 of the upper module M2, and the modules M1, M2 may be detached from each other by a user pressing the lever.

A needle channel bundle B having a plurality of needle channels 2200 coupled in the form of a bundle is rotatably disposed in the lower case 40 of the lower module M1 to be used to transplant hair roots (hair follicles). The needle channel bundle B may include a cylindrical center shaft 2100 and the plurality of needle channels 2200 radially arranged on the outer circumference of the center shaft 2100 at equal intervals.

A channel rotation unit for rotating the needle channel bundle by a predetermined angle corresponding to one channel is disposed on an upper portion of the needle channel bundle. In the illustrated embodiment, the channel rotation unit may include a first driving motor 2300 for rotating the center shaft 2100 of the needle channel bundle. A driving shaft of the first driving motor 2300 is mounted to be aligned with a center axis of the center shaft 2100 by means of a polygonal position determination pin 2320, and accordingly, the needle channel bundle B is rotated by driving of the first driving motor 2300.

The first driving motor 2300 may be implemented by using a step motor, for example, and may rotate the needle channel bundle B by a predetermined angle. In an embodiment, the needle channel bundle B may be rotated by the first driving motor 2300 by an angle corresponding to an interval of one needle channel 2200 at a time. For example, in the illustrated embodiment, 18 needle channels 2200 may be attached to the outer circumference of the center shaft 2100, and in this case, the first driving motor 2300 may be configured to rotate the needle channel bundle B by 20 degrees at a time by a single driving operation.

In an embodiment, a ball plunger 2450 (see FIG. 25) may be disposed on an upper surface of the needle channel bundle B in contact therewith to allow the needle channel bundle B to be rotated by a predetermined angle at a time. The ball plunger 2450 is coupled to and supported on a ball plunger support portion 2400 disposed on the upper portion of the needle channel bundle B. A detailed configuration of the ball plunger 2450 will be described below with reference to FIGS. 25 and 26.

A core shaft locking portion 2700 is disposed on a side surface of the lower case 40. The core shaft locking portion 2700 has a function of temporarily stopping a movement of a core shaft 2230 (see FIGS. 23A and 23B) slidably disposed in the needle channel 2200 by locking the core shaft 2230. A detailed configuration of the core shaft locking portion 2700 will be described below with reference to FIGS. 27 and 28.

The lower cap 50 is attachably and detachably coupled to the lower end of the lower case 40 to cover the lower end of the lower case 40. The lower cap 50 has a nozzle 51 formed on a lower surface thereof to allow one needle channel 2200 to pass therethrough, such that one needle channel 2200 can protrude to a predetermined length through the nozzle 51.

The upper module M2 is cased by the upper case 60 and the upper cap 70 and the bracket 2600 which are attached to the upper end and the lower end of the upper case 60, respectively.

The upper module M2 includes a push driving portion 2500 for pushing down one needle channel to let the needle channel protrude through the nozzle 51. In an embodiment, the push driving portion 2500 may include a second driving motor 2510, a gear box 2520, a lead screw 2530, a sliding block 2540, and a push bar 2550.

The second driving motor 2510 is implemented by using a certain motor rotating bidirectionally and having a driving shaft. The driving shaft of the second driving motor 2510 is coupled to the gear box 2520, and an output end rotary shaft of the gear box 2520 is coupled to the lead screw 2530 through a coupling 2525. Screw threads are formed on the outer circumference of the lead screw 2530. The sliding block 2540 is coupled to the lead screw 2530 to be movable up and down by the rotation of the lead screw 2530. The push bar 2550 is a pole-shaped member and has an upper end coupled to the sliding block 2540 and fixed thereto and extends downward therefrom As can be seen from the drawings, the push bar 2550 and the nozzle 51 are aligned in the same vertical line. Accordingly, the push bar 2550 is moved down by driving of the second driving motor 2510 and pushes down one needle channel 2200 positioned in the same vertical line, and the pushed needle channel 220 protrudes to a predetermined length through the nozzle 51.

Since the hair transplanter according to an embodiment includes only the two driving motors 2300, 2510 in the cases 40, 60, a margin space increases in the cases in comparison to the related-art hair transplanter using three motors. Accordingly, since a higher performance motor can be used as the second driving motor 2510 in comparison with the related-art hair transplanter, a distance (pitch) between the screw threads on the lead screw 2530 can be further increased in comparison to the related-art hair transplanter. For example, a pitch between screw threads of a related-art lead screw is about 1 mm, whereas the pitch distance between the screw threads of the lead screw 2530 may be designed to 24 mm according to an embodiment.

As described above, since the pitch distance of the lead screw 2530 is 24 times longer than that of the related-art lead screw when only the pitch distances are compared, an advancing direction of the sliding block 240 which advances when the lead screw 2530 is rotated a single time is about 10 times longer than in the related-art hair transplanter, even if a difference in the design of the coupling 2525 or the gear box 2520 is considered. Accordingly, since the sliding speed of the push bar 2550 is about ten times higher than in the related-art hair transplanter, the total time required to perform hair transplantation can be reduced, and a technical effect of reducing operator's force required to perform hair transplantation can be achieved. That is, every time the needle channels 2200 are inserted into a scalp one by one during a real operation procedure, the operator should use a force to fix the hair transplanter to prevent it from shaking. For example, if it is assumed that it takes 1 second to insert one needle channel into a scalp and to draw out the same using the related-art hair transplanter, these operations may be completed within 0.1 second by using the hair transplanter of the present disclosure. That is, the total time required to perform the operation procedure can be reduced, and also, the time required to use the force by the user can be reduced accordingly, and the degree of fatigue that the user feels during the operation procedure can be reduced.

A power line and a control line may be connected to the upper module M2 form the outside to apply power to the push driving unit 2500 and to control the operation, and to achieve this, a wiring connector 65 is formed on the upper module M2. In addition, although not shown, a power line and/or control line may be connected to the lower module M1 from the outside to rotate the needle channel bundle B, and to achieve this, a wiring connector (not shown) may be formed on the lower module M1. In addition, a balance arm with a brake device may be connected to a balance arm connector 75 of the upper cap 70 to control a repulsive force and to compensate for a weight.

Figure 22:
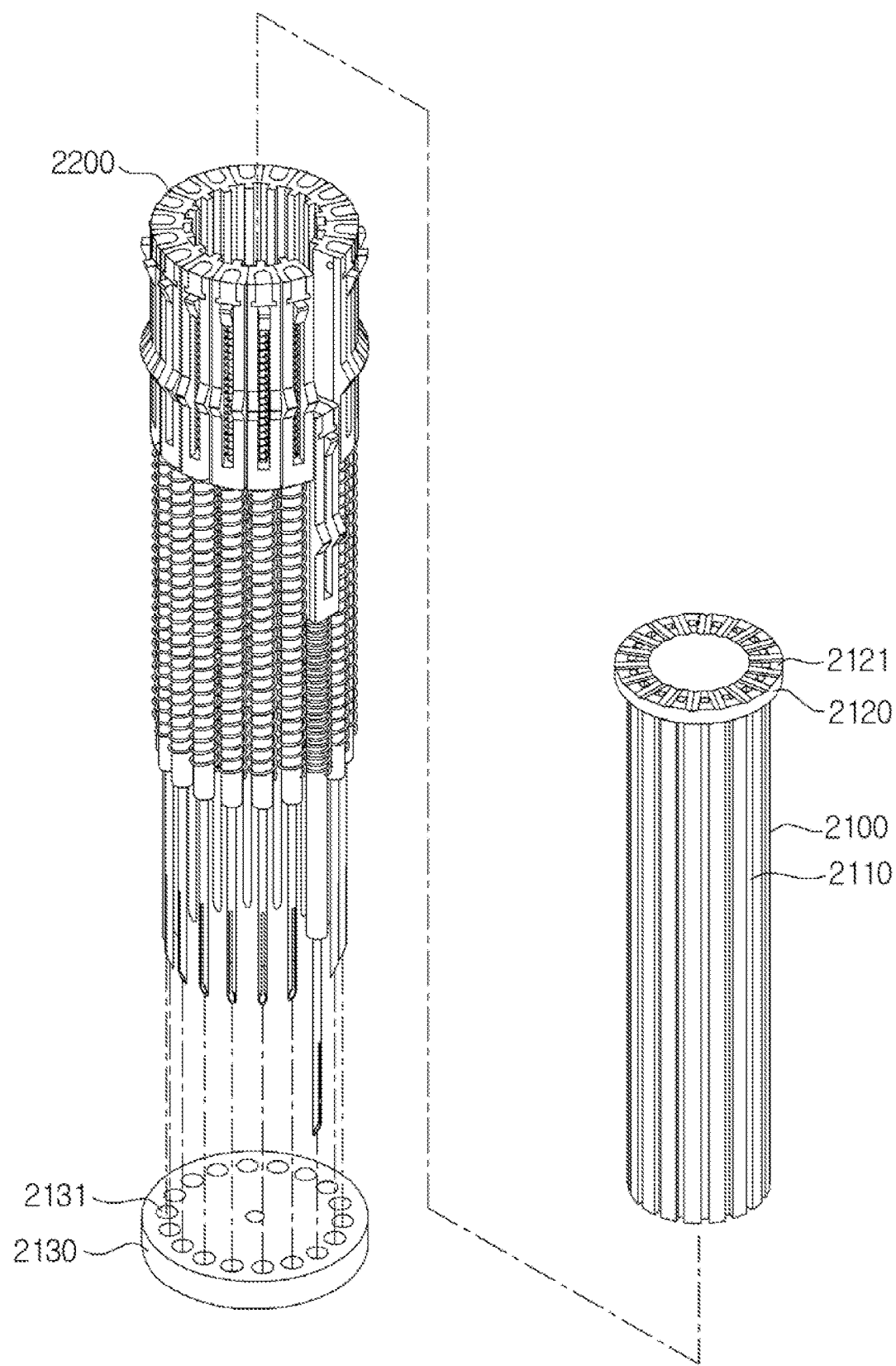
FIG. 22 is a view to illustrate a needle channel bundle according to an embodiment.

FIG. 22 is a view to illustrate the needle channel bundle B according to an embodiment. Referring to the drawing, the needle channel bundle B includes the center shaft 2100 and the plurality of needle channels 2200 coupled to the outer circumference of the center shaft 2100 to be slidable up and down.

A plurality of slide rails 2110 are formed on the outer circumference of the center shaft 2100 radially at equal intervals with reference to a center axis of the center shaft. In an embodiment, the slide rails 2110 are recessed lengthways in the vertical direction.

A flange 2120 having a larger diameter than a diameter of the center shaft 2100 is formed on the upper end of the center shaft 2100. The flange 2120 may be integrally formed with the center shaft 2100, or may be separately formed and may be attached to the upper end of the center shaft 2100. Since the flange 2120 having the large diameter is positioned on the upper end of the center shaft 2100, the needle channels 2200 do not move up further, and accordingly, the flange 2120 may serve as a stopper for restricting an upward sliding movement range of the needle channel 2200.

Figure 23A:
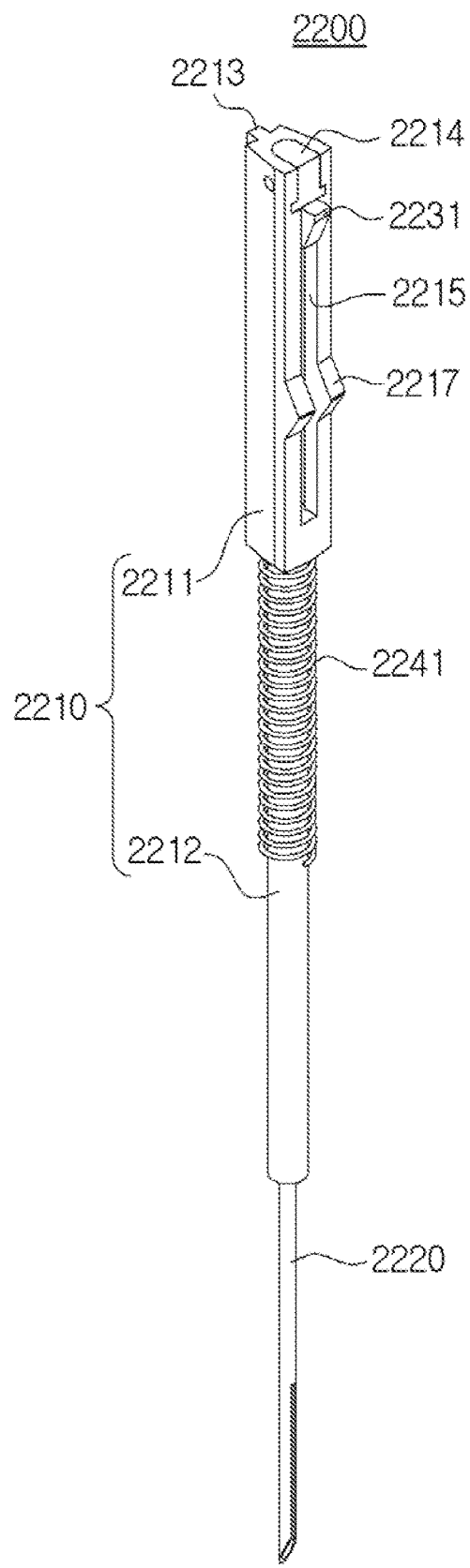
FIGS. 23A and 23B are a perspective view and a cross sectional view of the needle channel according to an embodiment.
Figure 23B:
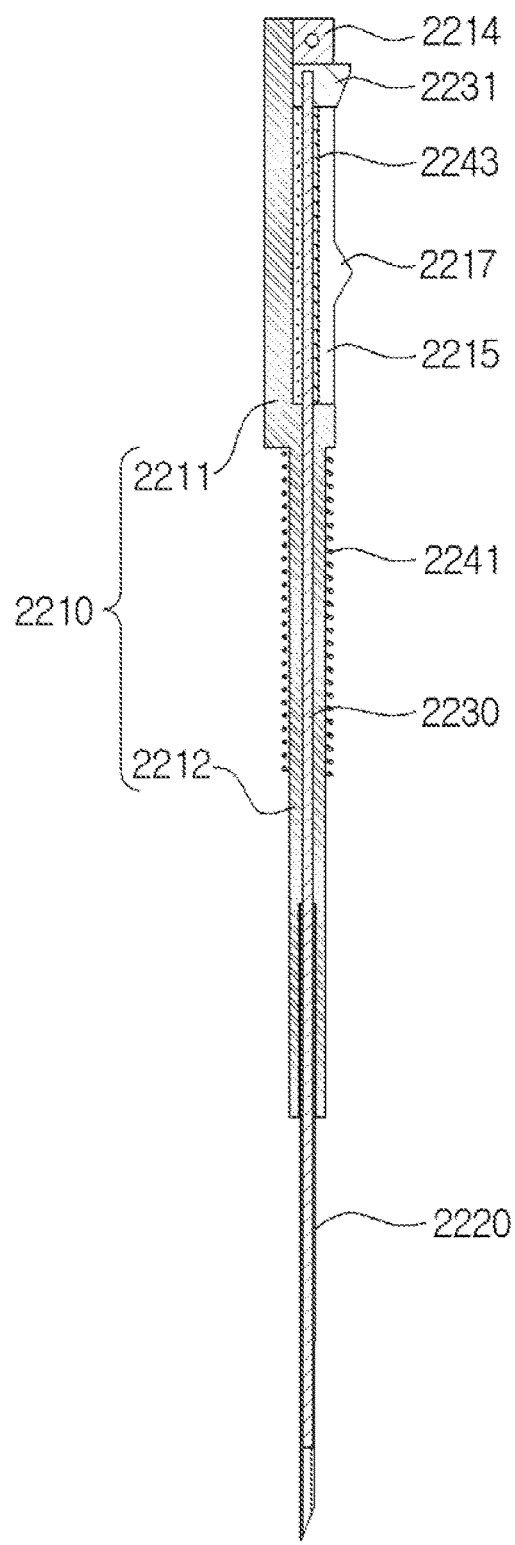
Figure 24:
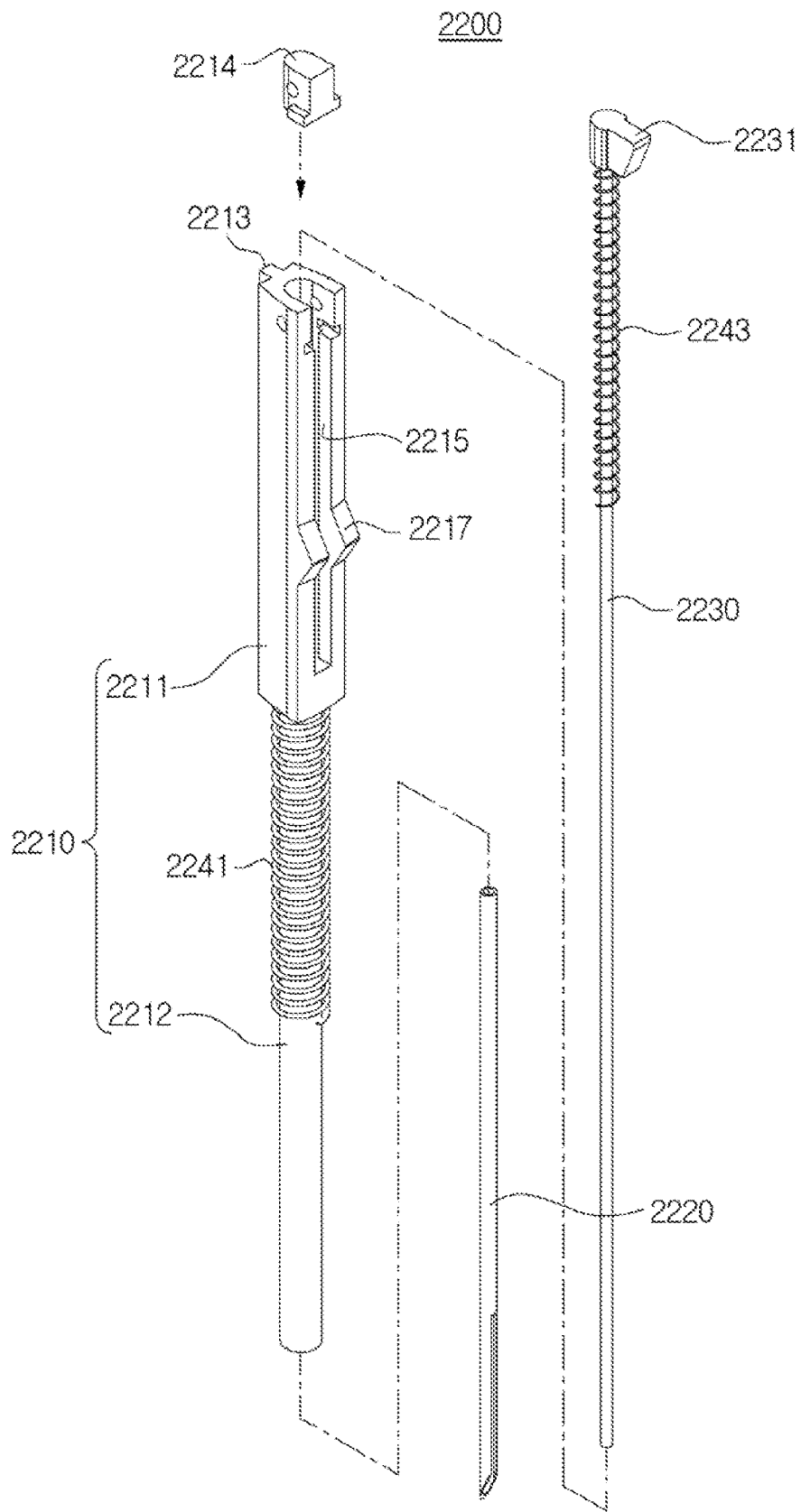
FIG. 24 is an exploded perspective view of the needle channel according to an embodiment.

FIGS. 23A and 23B and FIG. 24 are views illustrating the needle channel 2200. Specifically, FIG. 23A is a perspective view of the needle channel 2200, FIG. 23B is a cross-sectional view, and FIG. 24 is an exploded perspective view of the needle channel 2200.

Referring to the drawings, the needle channel 2200 may include a body 2210 having a tubular inner space formed therein, a needle 2220 coupled to a lower portion of the body 2210, and the core shaft 2230 slidably disposed in the tubular inner space.

The body 2210 may include an upper body 2211 and a lower body 2212 which have different cross-section areas. In the illustrated embodiment, the lower body 2212 has a smaller cross-section area than that of the upper body 2211, and accordingly, there is a stepped portion on a connection portion between the upper body 2211 and the lower body 2212.

The upper body 2211 and the lower body 2212 may be separately fabricated and may be coupled to each other, or the upper body 2211 and the lower body 2212 may be integrally formed with each other. The lower body 2212 may have a tubular inner space formed therein, and may have a lower end opened. The needle 2220 for transplanting hair roots is inserted and coupled through the opened lower end of the lower body 2212, and the core shaft 2230 is slidably disposed in the inner space of the lower body 2212.

The upper body 2211 includes a side surface protrusion 2213 formed on one side surface thereof lengthwise in the vertical direction. The side surface protrusion 2213 protrudes toward the center shaft 2100, that is, in the inward radial direction, and has a protruding shape to be engaged with the recess portion of the slide rail 2110 of the center shaft 2100. Accordingly, the side surface protrusion 2213 of the upper body 2211 is inserted into the slid rail 2210 of the center shaft 2100, such that the needle channel 2200 can slide up and down along the slid rail 2110.

The configuration in which the needle channels 2200 are arranged on the whole outer circumference of the center shaft 2100 radially at equal intervals, and are coupled to the center shaft 2100 is the same as or similar to the configuration of the first embodiment described above with reference to FIG. 8, etc.

The needle channel 2200 includes a first spring 2241 fitted over the body 2210. In the illustrated embodiment, the first spring 2241 is fitted over the circumference of the lower body 2212, and accordingly, the upper end of the first spring 2241 is supported on the stepped portion between the upper body 2211 and the lower body 2212 of the needle channel.

As shown in FIG. 22, the needle channel bundle B includes a needle channel support plate 2130 having a plurality of penetrating holes 2131 formed thereon to allow the lower bodies of the plurality of needle channels 2200 coupled to the needle channel bundle B to penetrate therethrough, respectively.

The needle channel support plate 2130 has a disk shape of a predetermined thickness, and the lower bodies 2212 of the needle channels 2200 pass through the respective penetrating holes 2131 and are inserted into the needle channel support plate 2130. A diameter of each penetrating hole 2131 is larger than the diameter of the lower body 2212 and is smaller than the diameter of the first spring 2241. Therefore, the lower end of the first spring 2241 is supported on the upper surface of the needle channel support plate 2130.

The needle channel support plate 2130 is rotatably supported on an upper portion of an annular support member 42 (see FIG. 21) fixed to an inner wall of the lower case 40, and may be coupled to or decoupled from the center shaft 2100. Accordingly, the needle channel support plate 2130 may elastically support the needle channel bundle B through the first springs 2241, and the needle channel bundle B and the needle channel support plate 2130 are integrally rotated by the first driving motor 2300.

In the illustrated embodiment, the body 2210 includes the upper body 2211 and the lower body 2212 having different diameters. However, in an alternative embodiment, the lower body 2212 may be omitted. In the alternative embodiment, the needle 2220 may be coupled to the upper body 2211 and the first spring 2241 may be fitted over the circumference of the needle 2220. In this case, the upper end of the first spring 2241 may be supported on the lower end of the upper body 2211, and the lower end of the first spring 2241 may be supported on the upper surface of the needle channel support plate 2130.

When the push bar 2550 pushes down one needle channel 2200 by the second driving motor 2510, the needle channel 220 is moved down and the first spring 2241 is compressed. When the push bar 2550 moves up, the needle channel 2200 moves up due to the elastic force of the compressed first spring 2241.

As shown in FIGS. 23A and 23B and FIG. 24, a slot 2215 is formed on a side surface of the upper body 2211 of the needle channel 2200 facing in the outward radial direction, lengthwise in the vertical direction. That is, the side surface protrusion 2213 and the slot 2215 of the upper body 2211 are formed on the opposite surfaces. The upper portion of the slot 2215 may be blocked by an upper cover 2214 coupled to the upper end of the upper body 2211, and the lower portion of the slot 2215 fluidly communicates with the tubular inner space of the lower body 2212.

A lever 2231 is disposed in the slot 2215 to be slidable up and down along the slot 2215, and one side surface of the lever 2231 further protrudes to the outside (that is, in the outward radial direction) than the slot 2215. The upper end of the core shaft 2230 is coupled to the lever 2231, and accordingly, the lever 2231 and the core shaft 2230 may integrally slide up and down.

A second spring 2243 is fitted over the circumference of the core shaft 2230 in the slot 2215. The upper end of the second spring 2243 is supported on the lower surface of the lever 2231, and the lower end of the second spring 2243 is supported on the bottom surface of the slot 2215. Accordingly, when a force is applied to the lever 2231 and the lever 2231 and the core shaft 2230 move down, the second spring 2242 may be compressed, and when the force applied to the lever 2231 is removed, the core shaft 2230 moves up due to the elastic force of the second spring 2243.

Figure 25:
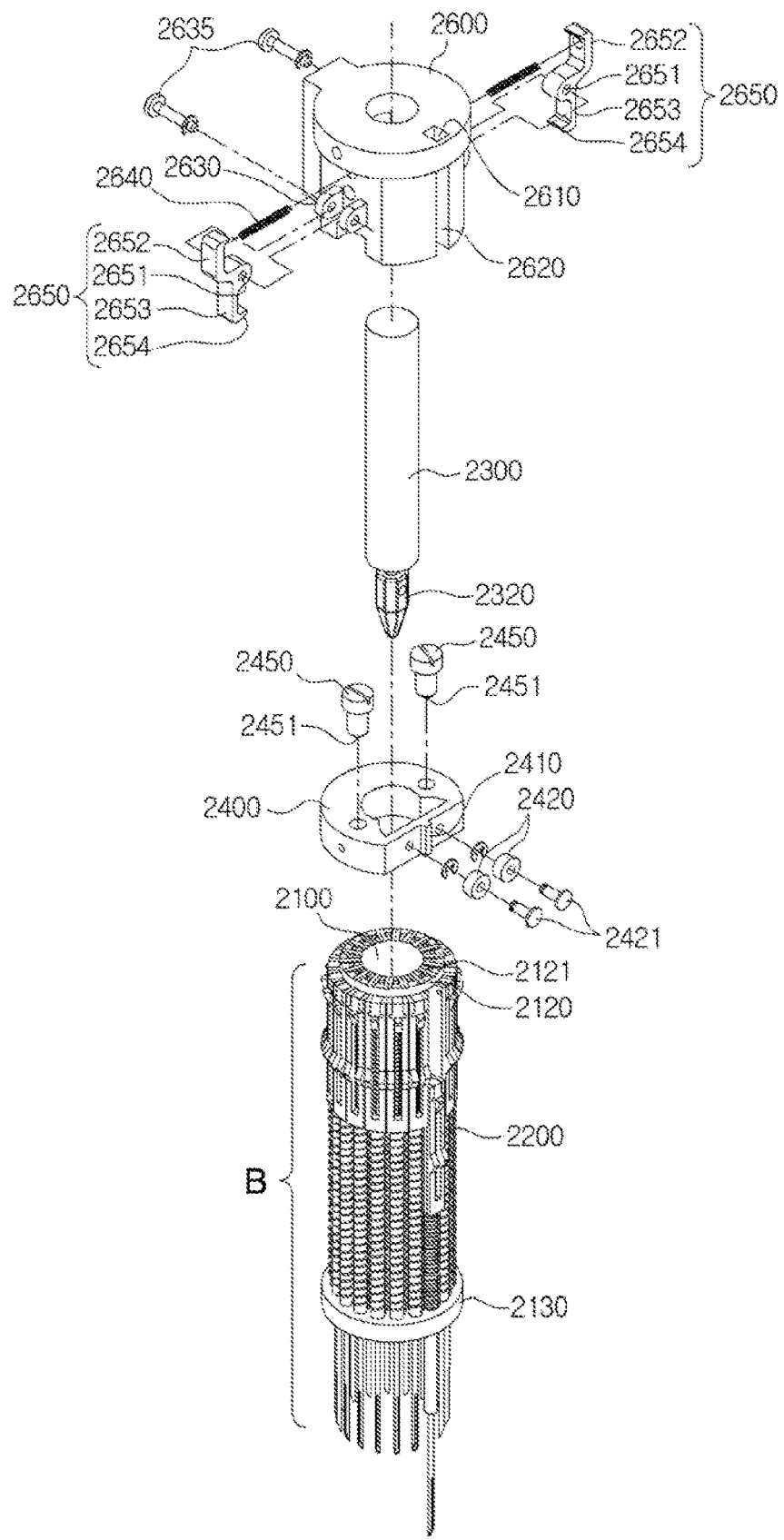
FIG. 25 is an exploded perspective view of some elements of the hair transplanter according to an embodiment.

FIG. 25 is an exploded perspective view of some elements of the hair transplanter. Referring to FIG. 25, the bracket 2600 has a substantially cylindrical shape having an inner space therein, and an upper portion of the bracket 2600 is fixed to the lower end of the upper case 60 to form a part of the upper module M2.

The bracket 2600 has a penetrating hole 2610 formed on the upper surface thereof to allow the push bar 2550 to penetrate therethrough, and has a guide recess 2620 formed on one side surface of the bracket 2600 to guide the push bar 2550.

Module coupling portions 2650 are installed on both side surfaces of the bracket 2600 to be coupled with the lower module M1. A well-known coupling method may be used to couple the lower module M1 and the upper module M2, and in the illustrated embodiment, the module coupling portion 2650 may include a hinge coupling portion 2651, an upper lever 2652 and a lower lever 2653 extending upward and downward from the hinge coupling portion 2651, and an engagement protrusion 2654 extending from a lower end of the lower lever 2653 and bending inward.

The hinge coupling portion 2651 is hinged to a hinge base 2630 on the side surface of the bracket 2600 by means of a fastening unit such as a bolt 2635, and the upper lever 2652 and/or the lower lever 2653 may be coupled to the bracket 2600 by means of an elastic member 2640. The engagement protrusion 2654 may be inserted into an engagement recess 43 (see FIG. 21) of the lower case 40, for example. Accordingly, when an external force is not applied, the engagement protrusion 2654 is inserted into the engagement recess 43, such that the lower module M1 and the upper module M2 are coupled to each other, and, when the user applies a force by pressing the upper lever 2652, the engagement protrusion 2654 is disengaged from the engagement recess 43, such that the lower module M1 and the upper module M2 may be decoupled from each other.

The ball plunger support portion 2400 may be coupled to the lower portion of the bracket 2600. The ball plunger support portion 2400 has an annular shape having a predetermined thickness, and the first driving motor 2300 may penetrate through a penetrating region in the middle of the ball plunger support portion 2400. The ball plunger support portion 2400 may have one side surface cut not to interfere with the movement of the push bar 2550, and may have a guide portion 2410 and a guide roller 2420 formed on the cut one side surface to guide the push bar 2550.

Figure 26:
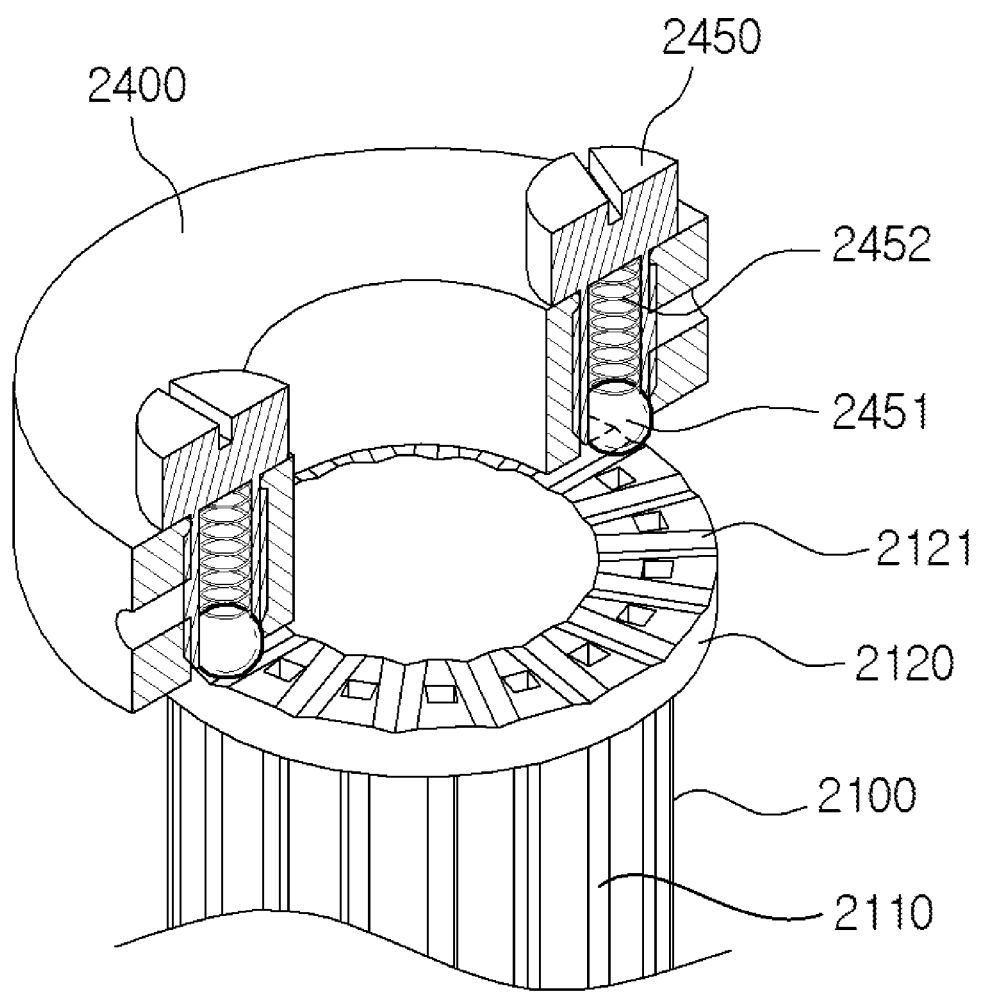
FIG. 26 is a view to illustrate a ball plunger support portion according to an embodiment.

Referring to FIGS. 25 and 26, the ball plunger support portion 2400 includes at least one ball plunger 2450 having a ball 2451 protruding downward therefrom. The ball plunger 2450 may include the ball 2451 having a part thereof exposed downward, and an elastic member 2452 disposed in the inner space of the ball plunger 2450 to elastically support the ball 2451. In the drawings, two ball plungers 2450 are illustrated, but the number or installation positions of the ball plungers 2450 are not limited.

In an embodiment, the upper surface of the center shaft 2100, that is, the upper surface of the flange 2120, may have a convex-concave shape 2121. That is, a concave portion and a convex portion may be alternately formed on the upper surface of the flange 2120, and the concave portion is formed at each upper position of the needle channel 220 in the vertical direction.

The ball plunger support portion 2400 is arranged such that the ball 2451 of the ball plunger 2450 comes into contact with the concave-convex shape of the flange 2120 and elastically presses the convex-concave surface. Accordingly, since the ball 2451 acts to be seated on the concave portion of the flange 2120 due to the elastic force of the elastic member 2452, it is guaranteed that the needle channel bundle B is regularly rotated by a predetermined angle at a time.

The core shaft locking portion 2700 is disposed on one side surface of the lower case 40 as shown in FIGS. 19 to 21. The core shaft locking portion 2700 functions to temporarily stop the ascending movement of the core shaft 2230 in the needle channel 2200 while the needle channel 2200 is moving up again after being pushed down by the push bar 2550.

Figure 27:
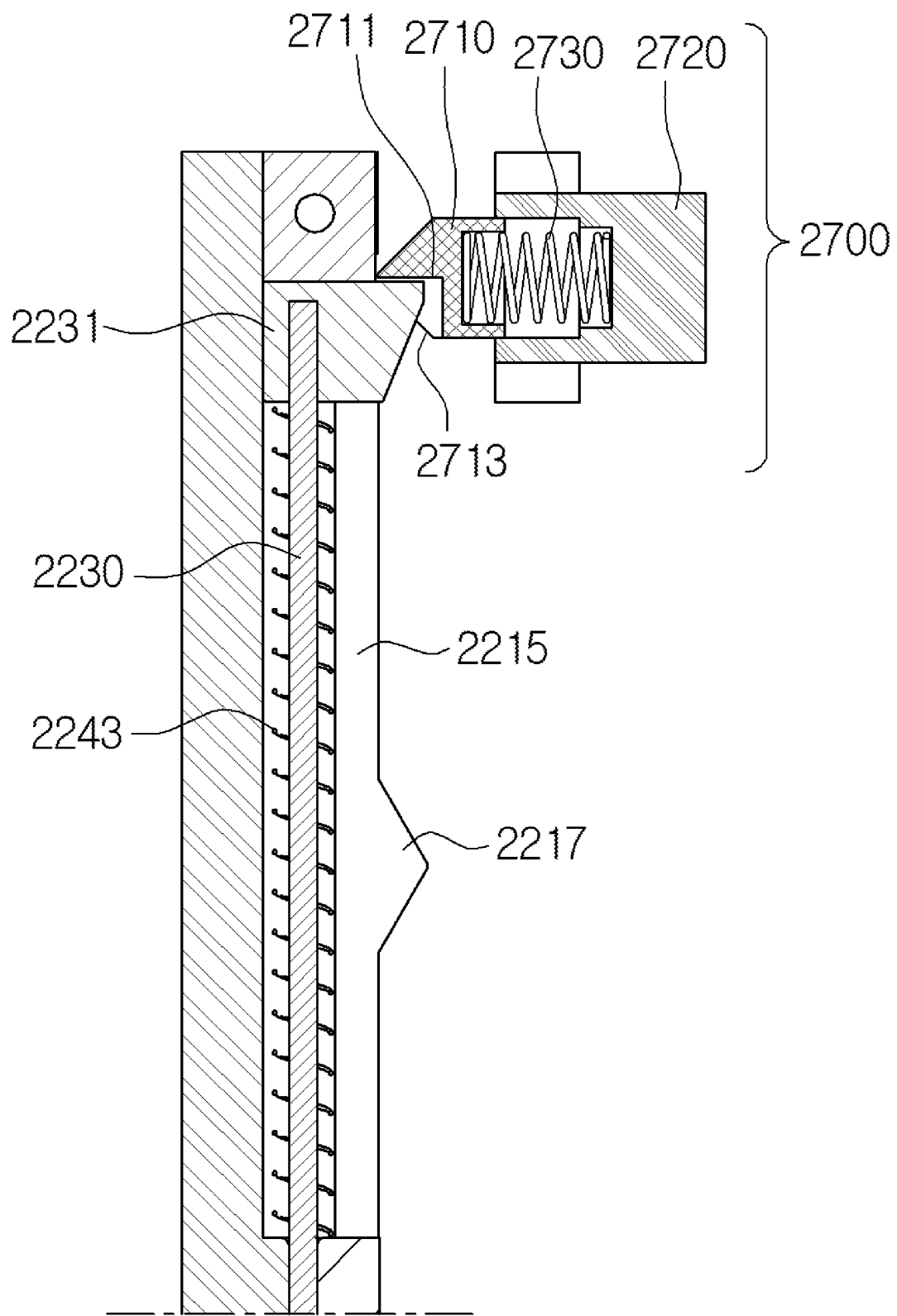
FIG. 27 is a cross-sectional view of a core shaft locking portion according to an embodiment.
Figure 28:
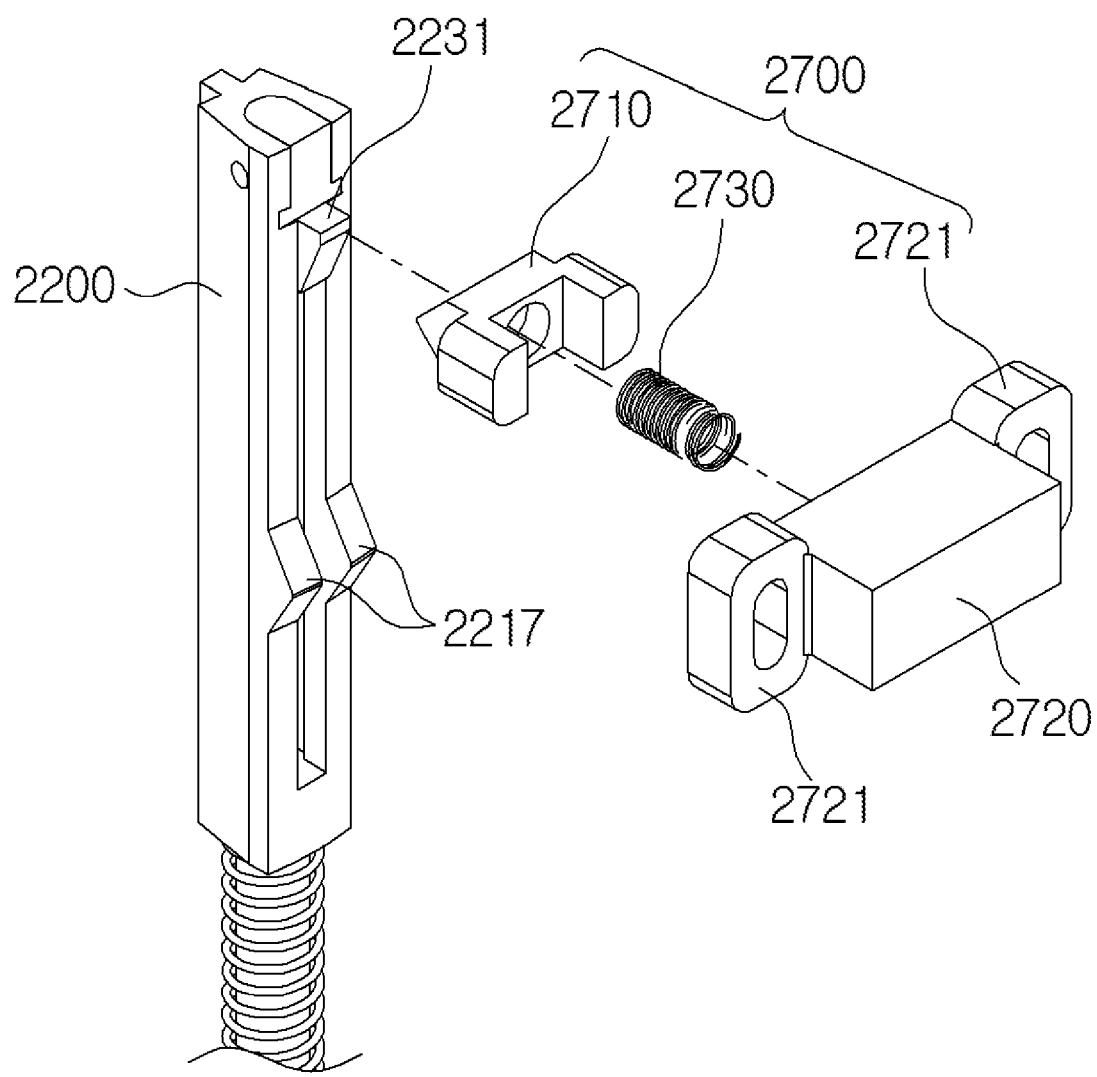
FIG. 28 is an exploded perspective view of the core shaft locking portion according to an embodiment.

Referring to FIGS. 27 and 28, the core shaft locking portion 2700 according to an embodiment may include a latch 2710, a latch receiving portion 2720 for receiving the latch 2710, and an elastic member 2730 interposed between the latch 2710 and the latch receiving portion 2720.

The latch receiving portion 2720 may be coupled and fixed to one side surface of the lower case 40 by means of bolts through bolt holes of extension regions 2721 formed on left and right sides thereof. The latch receiving portion 2720 has a space to receive the latch 2710 therein, and the elastic member 2730 such as a spring is interposed in this space. Accordingly, the latch 2710 is disposed within a distance to interfere with the vertical movement of the lever 2231, and is configured to elastically retract in the outward radial direction of the needle channel bundle B.

The core shaft locking portion 2700 according to the second embodiment is the same as or similar to the core shaft locking portion 1700 of the first embodiment described with reference to FIG. 10, and locks and unlocks the core shaft 2230 in the same or similar method as or to the method described above with reference to FIG. 11, and thus a detailed description will be omitted.

Figure 29:
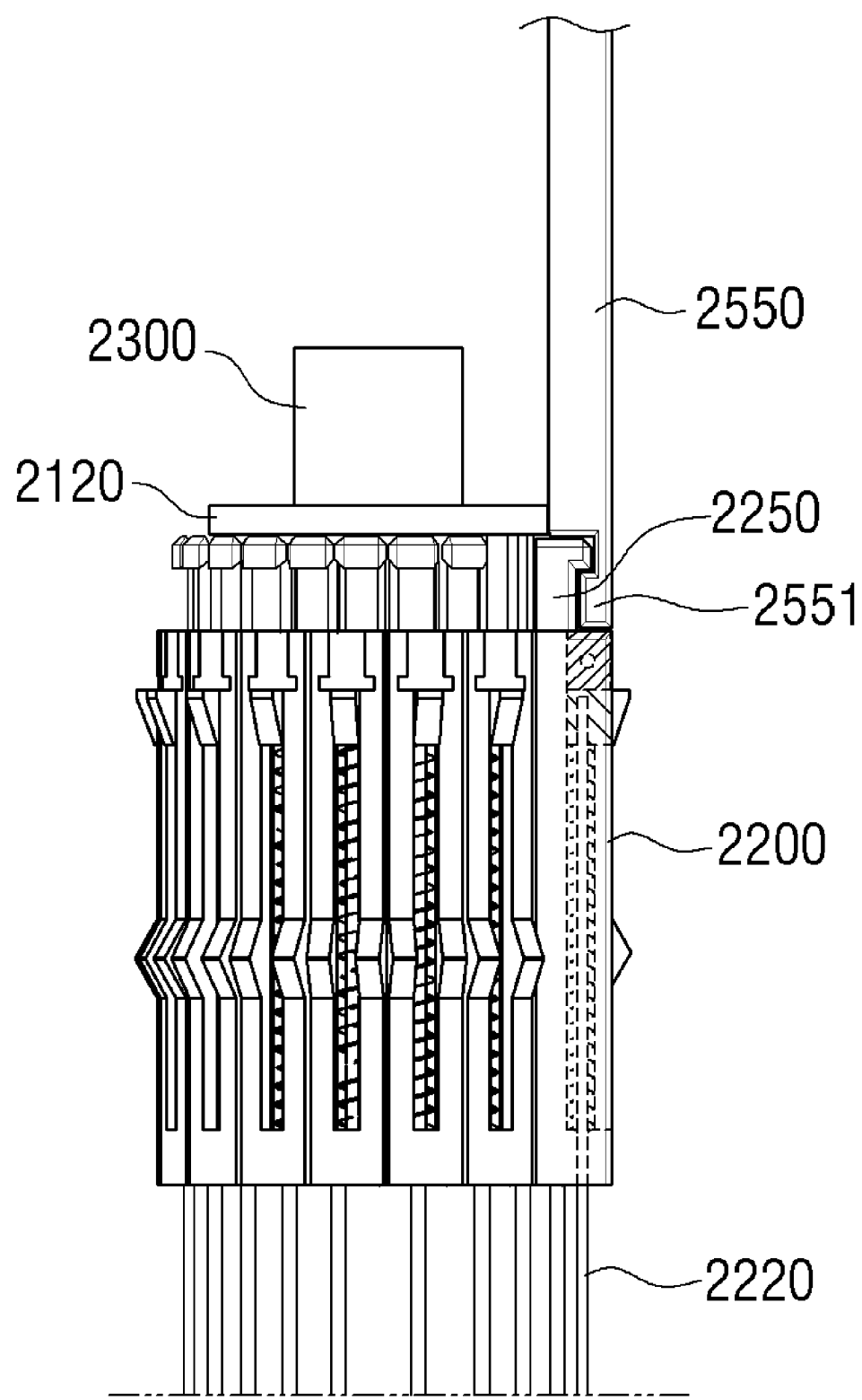
FIG. 29 is a view to illustrate a push bar and a needle channel according to an alternative embodiment.

FIG. 29 illustrates a push bar and a needle channel according to an alternative embodiment.

In the alternative embodiment, a first locking portion 2250 is formed on an upper end of the needle channel 2200. The first locking portion 2250 may be integrally formed with the body 2210 or may be integrally formed with the upper cover 2214. In addition, a second locking portion 2551 may be formed on a lower end of the push bar 2550 to be engaged with the first locking portion 2250 and to be locked.

The first locking portion 2250 and the second locking portion 2251 are formed to be engaged with each other only in the vertical direction. For example, as shown in the drawing, concave-convex structures are formed on the first locking portion 2250 and the second locking portion 2551, respectively, in the vertical direction, and the concave-convex structures of the two locking portions 2250, 2551 are engaged with each other, such that the two locking portions are locked into each other. Accordingly, the needle channel bundle may be rotated without being interfered by the second locking portion 2251 of the push bar 2550.

According to the above-described configuration, when one needle channel 2200 is aligned in the same vertical line as the push bar 2550 by the rotation of the needle channel bundle, the first locking portion 2250 of the needle channel 2200 and the second locking portion 2551 of the push bar 2550 are engaged with each other, and the needle channel 2200 is moved up and down integrally with the push bar 2550. Accordingly, according to the alternative embodiment, since the ascending operation of the needle channel 2200 is performed by the push bar 2550, a spring (2241 of FIG. 24) for moving up the needle channel 2200 is not required and thus the device structure can be more simplified.

While the invention has been shown and described with reference to certain preferred embodiments thereof, it will be understood by those skilled in the art that various changes in form and details may be made therein without departing from the spirit and scope of the invention as defined by the appended claims. Therefore, the scope of the invention is defined not by the detailed description of the invention but by the appended claims, and all differences within the scope will be construed as being included in the present invention.

What is claimed is:

1. A needle channel usable in a hair transplanter, the needle channel being configured to be coupled to an outer circumference of a center shaft in the hair transplanter to be slidable up and down, the needle channel comprising:
    a body having a tubular inner space formed therein;
    a needle coupled to a lower end of the body;

a core shaft slidably disposed in the tubular inner space and the needle;

a slot formed on the body in a longitudinal direction and opened in an outward radial direction from a center axis of the center shaft;

a lever coupled to an upper end of the core shaft, and disposed to be slidable up and down in the slot;

a spring fitted over a circumference of the core shaft and having an upper end supported on the lever and a lower end supported on a bottom surface of the slot, a locking protrusion protruding from the body in the outward radial direction and formed to surround the slot on the left and right; and a saw-toothed ratchet gear tooth formed at a lower end of the locking protrusion and having an inclination angle only in one direction.

2. The needle channel of claim 1, further comprising a locking recess of a concave structure formed on a surface of the body that faces in the outward radial direction under the locking protrusion, wherein, when the needle channel is mounted in the hair transplanter, and the needle channel is locked into a latch of a needle channel locking portion coupled to a side surface of an elevation gear holder, the needle channel is configured to move in association with a vertical movement of the elevation gear holder.

3. The needle channel of claim 2, wherein a lower end surface of the locking recess of the needle channel is formed at a right angle, and a first side surface of two side surfaces of the locking recess, and an upper end surface are formed as inclined surfaces by being chamfered.

4. The needle channel of claim 3, wherein an edge of the body of the needle channel that is adjacent to a second side surface of the two side surfaces of the locking recess is rounded.

5. The needle channel of claim 1, further comprising a projection protruding from a surface of the locking protrusion of the needle channel in the outward radial direction.

6. The needle channel of claim 5, wherein, when the needle channel is mounted in the hair transplanter and is pushed down and then moves up, the lever of the needle channel is locked into a core shaft locking portion of the hair transplanter, and the lever and the core shaft temporarily stop moving up, and wherein, when the needle channel further moves up, the projection releases the locking operation of the core shaft locking portion, thereby allowing the lever and the core shaft to move up.

7. A needle channel bundle provided with a plurality of needle channels according to claim 1 and usable in the hair transplanter, the needle channel bundle comprising:

the center shaft disposed in the hair transplanter in the longitudinal direction; and the plurality of needle channels, wherein the plurality of needle channels are arranged on the outer circumference of the center shaft at equal intervals in a radial direction with reference to the center axis of the center shaft, and are coupled to the center shaft to be slidable up and down.

8. The needle channel bundle of claim 7, wherein, when the needle channel bundle is mounted in the hair transplanter, the needle channel bundle is disposed to be surrounded by a channel rotation unit for rotating about the center axis of the center shaft, and wherein the needle channel bundle is rotated by the channel rotation unit by a predetermined angle, such that one needle channel is positioned on a predetermined position per each rotation.

9. The needle channel bundle of claim 8, wherein the channel rotation unit comprises a cylindrical elevation gear holder surrounding the needle channel bundle in contact with an outer circumference of a portion of the body of the needle channel that is under the locking protrusion, and a cylindrical ratchet support holder surrounding the needle channel bundle in contact with an outer surface of the elevation gear holder, wherein the saw-toothed ratchet gear tooth is provided in plurality as saw-toothed ratchet gear teeth, wherein a same number of wedge-type protrusions as the number of the ratchet gear teeth provided on the needle channel bundle are continuously formed on an upper surface of the elevation gear holder, wherein saw-toothed ratchet gear recesses are formed on an upper surface of the ratchet support holder and each of the saw-toothed ratchet gear recesses has an inclination angle to be engaged with a corresponding ratchet gear tooth of the ratchet gear teeth, and wherein an uppermost end of each wedge-type protrusion is positioned between uppermost ends of a corresponding saw-toothed ratchet gear recess of the saw-toothed ratchet gear recesses.

10. The needle channel bundle of claim 9, wherein, when an external force is not applied, the ratchet gear teeth of the needle channel bundle are seated and supported on the ratchet gear recesses of the ratchet support holder, respectively, and the elevation gear holder is positioned under the ratchet support holder, wherein, when the elevation gear holder moves up until the wedge-type protrusions are higher than the ratchet gear recesses, the ratchet gear teeth slide down along inclined surfaces of the wedge-type protrusions, and the needle channel bundle is rotated by the predetermined angle, and, when the elevation gear holder moves down until the wedge-type protrusions are lower than the ratchet gear recesses, the ratchet gear teeth slide down along inclined surfaces of the ratchet gear recesses, and the needle channel bundle is configured to be rotated by the predetermined angle, such that the needle channel bundle is rotated by one channel by the ascending and descending operation of the elevation gear holder.

11. The needle channel bundle of claim 7, further comprising an upper cover attached to an upper portion of the slot of the needle channel, wherein an upper surface of the upper cover is an inclined surface that is inclined by a predetermined inclination angle in a rotation direction of the needle channel bundle.

* * * * *